(12) United States Patent
Gang et al.

(10) Patent No.: US 8,487,084 B2
(45) Date of Patent: Jul. 16, 2013

(54) DNA-GUIDED NANOPARTICLE ASSEMBLIES

(75) Inventors: Oleg Gang, South Setauket, NY (US); Dmytro Nykypanchuk, Westbury, NY (US); Mathew Maye, Binghampton, NY (US); Daniel van der Lelie, Shoreham, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 525 days.

(21) Appl. No.: 12/418,355

(22) Filed: Apr. 3, 2009

(65) Prior Publication Data
US 2009/0275465 A1 Nov. 5, 2009

Related U.S. Application Data

(63) Continuation of application No. PCT/US2007/021267, filed on Oct. 3, 2007.

(51) Int. Cl.
C07H 21/04 (2006.01)
(52) U.S. Cl.
USPC ......... 536/23.1; 536/24.2; 977/704; 977/728; 977/773; 977/795
(58) Field of Classification Search
None
See application file for complete search history.

(56) References Cited

U.S. PATENT DOCUMENTS

| 7,098,320 B1 | 8/2006 | Mirkin et al. | |
|---|---|---|---|
| 2002/0172953 A1* | 11/2002 | Mirkin et al. | 435/6 |
| 2004/0110220 A1 | 6/2004 | Mirkin et al. | |
| 2007/0072205 A1* | 3/2007 | Lu et al. | 435/6 |

FOREIGN PATENT DOCUMENTS

WO WO2005/029076 3/2005

OTHER PUBLICATIONS

Claridge et al "Directed assembly of discrete gold nanoparticle groupings using branched DNA scaffolds" Chem. Mater. Mar. 9, 2005, 17: 16-28-1635.*
Written Opinion of the International Searching Authority issued Feb. 23, 2009 in related international application PCT/US2007/021267.
Valignant, Marie-Pierre, et al., "Reversible Self-Assembly and Directed Assembly of DNA-linked Micrometer-sized Colloids," *PNAS*, Mar. 22, 2005, vol. 102, No. 12, pp. 4225-4229.
Sharma, J., et al., "DNA-Templated Self-Assembly of Two-Dimensional and Periodical Gold Nanoparticle Arrays," *Angew. Chem. Int. Ed.*, 2006, vol. 45, pp. 730-735, and supporting information pp. 1-8.
Kim, Anthony J., et al., "Engineering DNA-Mediated Colloidal Crystallization," *Langmuir*, 2006, vol. 22, No. 5, pp. 1991-2001.
Nykypanchuk, et al., "DNA-Guided Crystallization of Colloidal Nanoparticles," *Nature*, Jan. 31, 2008, vol. 451, pp. 549-552, and supplementary information pp. 1-7.

(Continued)

*Primary Examiner* — Betty Forman
(74) *Attorney, Agent, or Firm* — Dorene M. Price

(57) ABSTRACT

In some embodiments, DNA-capped nanoparticles are used to define a degree of crystalline order in assemblies thereof. In some embodiments, thermodynamically reversible and stable body-centered cubic (bcc) structures, with particles occupying <~10% of the unit cell, are formed. Designs and pathways amenable to the crystallization of particle assemblies are identified. In some embodiments, a plasmonic crystal is provided. In some aspects, a method for controlling the properties of particle assemblages is provided. In some embodiments a catalyst is formed from nanoparticles linked by nucleic acid sequences and forming an open crystal structure with catalytically active agents attached to the crystal on its surface or in interstices.

20 Claims, 16 Drawing Sheets

OTHER PUBLICATIONS

Tkachenko, Alexei V., "Morphological Diversity of DNA-Colloidal Self-Assembly," *Physical Review Letters*, Sep. 30, 2002, vol. 89, No. 14, pp. 148303-1-148303-4.

Alivisatos, Paul A., et al., "Organization of 'Nanocrystal Molecules' Using DNA," *Nature*, Aug. 15, 1996, vol. 382, pp. 609-611.

Freeman, R. Griffith, et al., "Ag-Clad Au Nanoparticles: Novel Aggregation, Optical, and Surface-Enhanced Raman Scattering Properties," *J. Phys. Chem.*, 1996, vol. 100, pp. 718-724.

Grützmacher, Detlev, et al., "Three-Dimensional Si/Ge Quantum Dot Crystals," *Nano Letters*, 2007, vol. 7, No. 10, pp. 3150-3156.

Lim, I-Im S., et al., "Assembly of Gold Nanoparticles Mediated by Multifunctional Fullerenes," *Langmuir*, 2007, vol. 23, pp. 10715-10724.

Lytton-Jean, Abigail K.R., et al., "A Thermodynamic Investigation into the Binding Properties of DNA Functionalized Gold Nanoparticle Probes and Molecular Fluorophore Probes," *J. Am. Chem. Soc.*, 2005, vol. 172, pp. 12754-12755, and supporting information pp. S1-S3.

Maye, Mathew M., et al., "A Simple Method for Kinetic Control of DNA-Induced Nanoparticle Assembly," *J. Am. Chem. Soc.*, 2006, vol. 128, pp. 14020-14021, and supporting information pp. S1-S10.

Mirkin, Chad A., "A DNA-Based Method for Rationally Assembling Nanoparticles into Macroscopic Materials," *Nature*, Aug. 15, 1996, vol. 382, pp. 607-609.

Nykypanchuk, Dmytro, et al., "DNA-Based Approach for Interparticle Interaction Control," *Langmuir*, 2007, vol. 23, pp. 6305-6314.

Park, So-Jung, et al., "The Structural Characterization of Oligonucleotide-Modified Gold Nanoparticle Networks Formed by DNA Hybridization," *J. Phys. Chem. B*, 2004, vol. 108, pp. 12375-12380.

Shevchenko, Elena, V., "Structural Diversity in Binary Nanoparticle Superlattices," *Nature*, Jan. 5, 2006, vol. 439, pp. 55-59, and supplementary information pp. 1-9.

Strouse, Geoffrey F., U.S. Army Report entitled, "Assembling Nano-Materials by BioScaffolding: Crystal Engineering in Nano-Electronics," Mar. 30, 2000.

Gilham, P., "The Synthesis of Polynucleotide-Celluloses and Their Use in the Fractionation of Polynucleotides," *Journal of the American Chemical Society*, vol. 86, pp. 4982-4985, 1964.

Tanaka, H. et al., "Visualization of Detailed Structures Within DNA," *Surface Science*, vol. 539, pp. L531-536, 2003.

Weaver, R., "Molecular Biology," Boston, WCB/McGraw-Hill, p. 758, 1999.

* cited by examiner

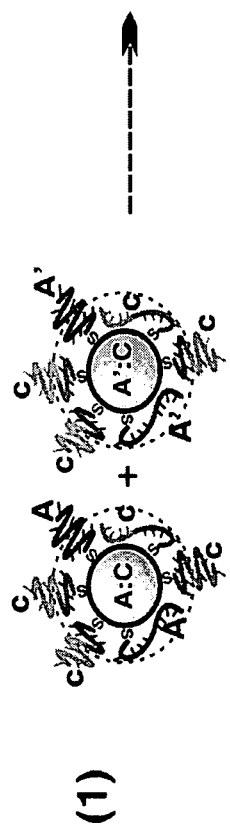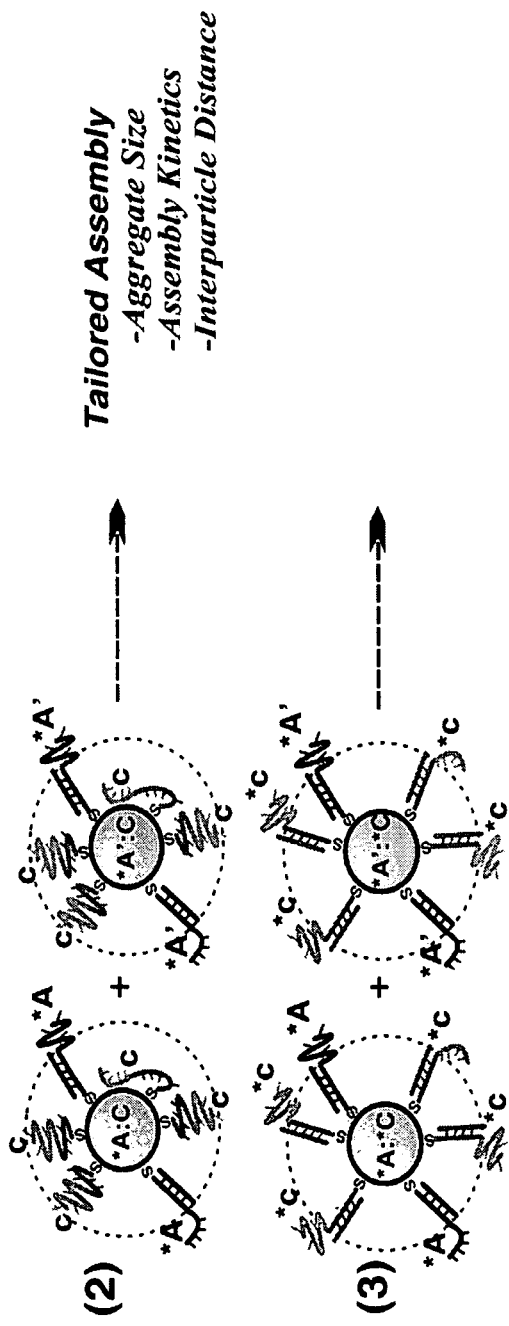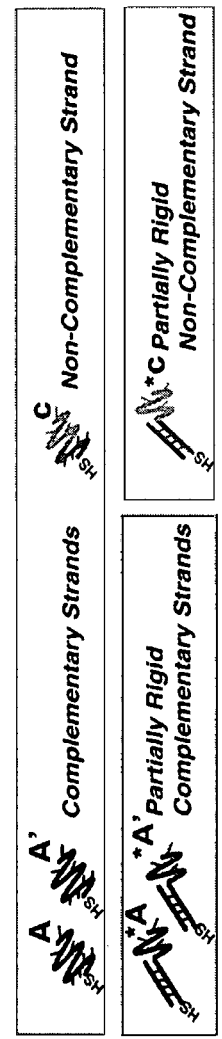
FIG. 3A
FIG. 3B
FIG. 3C

FIG. 5A
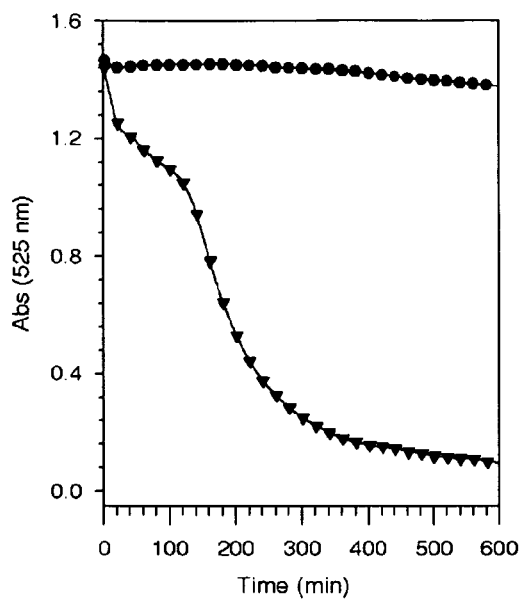
FIG. 5B
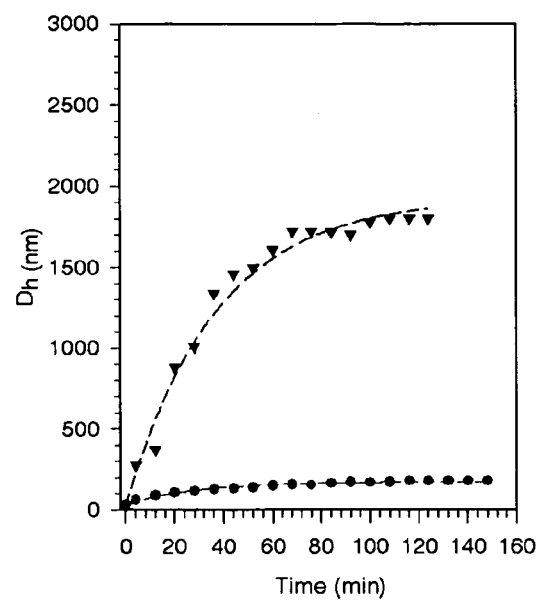
FIG. 5C
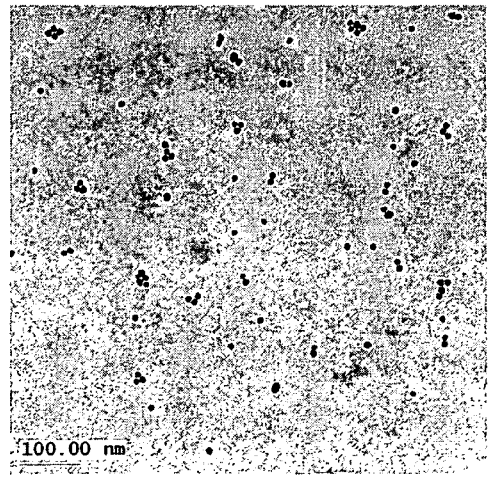
FIG. 5D
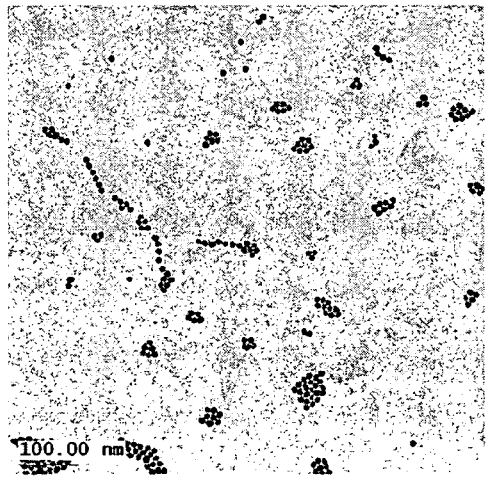
Fig. 5

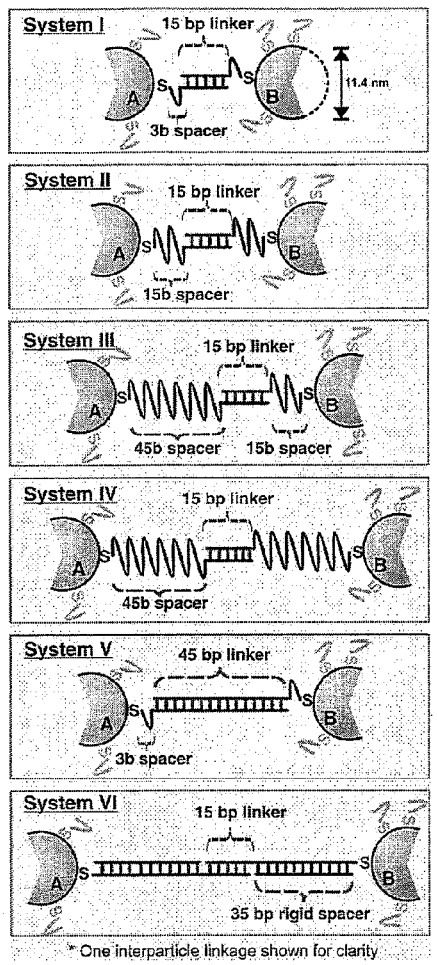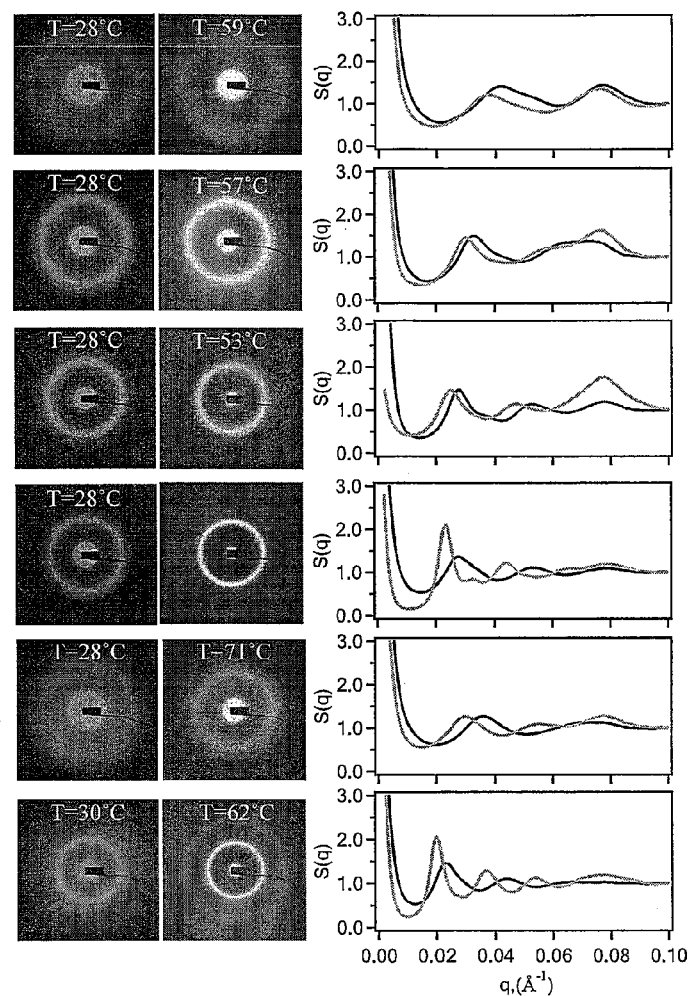
Fig. 6.　　　　Fig. 7　　　　Fig. 8

(a) (b)

DNA-GUIDED NANOPARTICLE ASSEMBLIES

This application is a continuation of International Application Number PCT/US2007/021267 filed Oct. 3, 2007, which claims the benefit of both U.S. Provisional Patent Application Ser. No. 60/849,451 filed Oct. 4, 2006 and U.S. Provisional Patent Application Ser. No. 60/957,543, filed Aug. 23, 2007. Each of these applications is incorporated herein by reference in its entirety.

This invention was made with Government support under contract number DE-AC02-98CH10886, awarded by the U.S. Department of Energy. The Government has certain rights in the invention.

BACKGROUND OF THE INVENTION

The invention relates to the field of DNA-guided particle assembly and, in particular, to three dimensional structuring of DNA-guided particle assemblies.

The ability to regulate the kinetic behavior of DNA-based nanosystems is required for emerging nanoparticle applications in sensing, nano-device assembling, and gene delivery. DNA based methodology takes advantage of the tunable and programmable hybridization between DNA-capped nanomaterials. This approach has allowed for the development of sensitive detection systems based on the optical and physical properties of assembled nanoparticles, as well as detection based on their novel melting/disassembly properties.

Currently, the self-assembly of metallic (gold, silver, platinum), semiconductive (CdSe, CdTe, CdSeZnS), and magnetic ($Fe_2O_3$, FePt) nanoparticles is separated into two classes, organic solvent based systems, and aqueous solution based systems. Each system has its advantages and disadvantages. In the organic solvent systems, nanoparticles are encapsulated with a dense shell of hydrophobic ligands (alkanethiol monolayers, polymers, multidentate ligands). The advantage of this class of nanoparticles is that the field is more mature, the particles are extremely stable, and a number of assembly routes for layer-by-layer assembly of nanoparticles on surfaces, or controlled aggregates in solution have been demonstrated. The disadvantage of this class is a lack of addressable chemistries at the nanoparticle surface, the harsh organic solvent environment (toluene, hexane, etc.), and the lack of tunable post-assembly structuring.

In contrast, while the use of aqueous based nanoparticle systems is not as mature, it may offer advantages over the organic solvent systems. First, it does not suffer from environmental concerns related to the solvent, and second, the systems allow for the functionalization of the nanoparticles with either biologically active or biologically mimicked surface encapsulation. For example, the ability of nature to self-assemble DNA, proteins, lipids, and extended hierarchies of multiple components is unrivaled by human synthetic capabilities.

Metamaterials are a class of ordered nanocomposites that exhibit exceptional properties not readily observed in nature. To benefit from their application in the fields of optics, magnetics, and medicine, three-dimensional structures created from individual nanoparticles are required. Current methods, including lithographic and traditional self-assembly approaches, are limited in their ability to fabricate three-dimensional structures with controllable order and particle-particle distance.

Precise positioning and ordered organization of nano-objects in three dimensions, a key to the creation of functional devices and new magnetic, plasmonic, and photonic metamaterials, is a challenging and actively developing frontier of nanoscience. Diverse self-assembled ordered phases have been observed for binary mixtures of uncapped nanoparticles as a result of the delicate interplay of geometrical factors, charges, and dipole and steric interactions. An alternative approach of using biomolecules to guide nanoparticle assembly is perceived to be advantageous due to the tunability of interparticle distances and assemblage structure. In addition, the addressability of bio-interactions may allow for rational creation of multi-component systems, while the rich energetic landscape of biomolecular conformations offers feasibility of dynamically reconfigurable systems. Some of these properties have been demonstrated with designed protein and DNA scaffolds, which have been employed to position nano-objects in one and two dimensions. The behavior of DNA functionalized micro- and nano-objects and their assembly in three dimensions has been the subject of extensive optical, structural and theoretical studies. However, long-range three-dimensional (3D) ordering via the addressable biological interactions has remained elusive.

SUMMARY

As these nucleic acid-functionalized systems allow for more sophisticated detection, and increasingly complex bottom-up construction, a protocol for the regulation of their assembly kinetics would be beneficial. In addition, the ability to tailor such assembly with relatively little synthetic workload, as well as the ability to perform experiments under environmentally benign conditions, i.e. aqueous solutions, would be extremely beneficial to the field.

Recognizing the desirability of controlling assembly kinetics and of creating metamaterials with long-range three-dimensional order through biological interactions, so-called "bio-inspired" metamaterials, certain embodiments of the invention provide such materials and methods for generating them.

In some embodiments the invention provides an assemblage of two types of particle functionalized with partially complementary sequences of DNA, and having long-range order. These particles may be nano-objects, micro-objects, or other forms of particle. In some embodiments, the functionalized particles are substantially non-interacting and are linked with a separate sequence of DNA having linking regions complementary to each of the two types of particles' DNA sequences. In some embodiments the particles are nanoparticles having dimensions of about 1 nm to about 100 nm. In some embodiments the particles are microparticles having dimensions of about 0.1 μm to about 100 μm. For some embodiments, methods for making such assemblies are described.

In some embodiments two types of particles interact through their functionalizing DNA to form assemblages. In some embodiments three or more types of particles form part of an assemblage. In some embodiments the assemblages are amorphous. In some embodiments the assemblages exhibit long-range crystalline order. Some instantiations may include both crystalline and amorphous regions.

In some embodiments, the properties of a particle assemblage are controlled by selecting the lengths of complementary and non-complementary segments of the DNA sequences. In some embodiments the ratio of complementary and non-complementary, or "neutral," DNA is specified to control certain properties of the assemblage. In some embodiments at least one segment of neutral region is double-stranded. In some embodiments, the properties controlled may be the melting temperature of the assemblage, the distance between particles in the assemblage, the degree of crystallinity of the assemblage, the crystal structure, and the like. In some embodiments the spacer comprises at least 5 bases of poly-T DNA and the neutral sequence of the linker comprises at least 5 bases of single-stranded poly-T DNA.

Some embodiments provide a method of making a metamaterial having long-range crystalline order using at least two types of DNA-capped particles linked along mutually complementary segments of the respective DNA sequences and not linked along non-complementary neutral segments of the DNA sequences. In some embodiments, a plasmonic crystal is formed from a metamaterial comprising two or more types of particle, of the same or different materials, linked along a linking region by mutually complementary segments of DNA that cap the particles, and not linked along regions of neutral segments of the DNA.

Some embodiments of the metamaterials made by the methods described herein offer very open crystal structures, with the functionalized particles occupying less than about ten percent of the volume of the crystal. In some embodiments these open structures are used as catalysts or as substrates for catalysts.

It should be understood that, in this context, "neutral" refers to the non-interacting nature of a DNA sequence and not to a distribution of charge.

It should also be understood that the foregoing, being a summary, is necessarily a brief description of some aspects of the invention, which may be better understood with reference to the drawings and the following detailed description.

BRIEF DESCRIPTION OF THE DRAWINGS

FIGS. 3A, 3B, and 3C depict an idealized illustration for the assembly between nanoparticles with both complementary and non-complementary ssDNA capping before and after hybridization.

FIGS. 5A, 5B, 5C, and 5D depict kinetic profiles, DLS results, and TEM images of assemblages comprising 85% and 95% neutral DNA.

FIG. 6 is a schematic view of the structure of DNA linkages between nanoparticles.

FIG. 7 shows small-angle X-ray scattering (SAXS) patterns for systems before annealing and after annealing at $T_{pm}$.

FIG. 8 shows extracted structure factors S(q) for scattering patterns shown in FIG. 7.

DETAILED DESCRIPTION

Figures 1A, 1B:
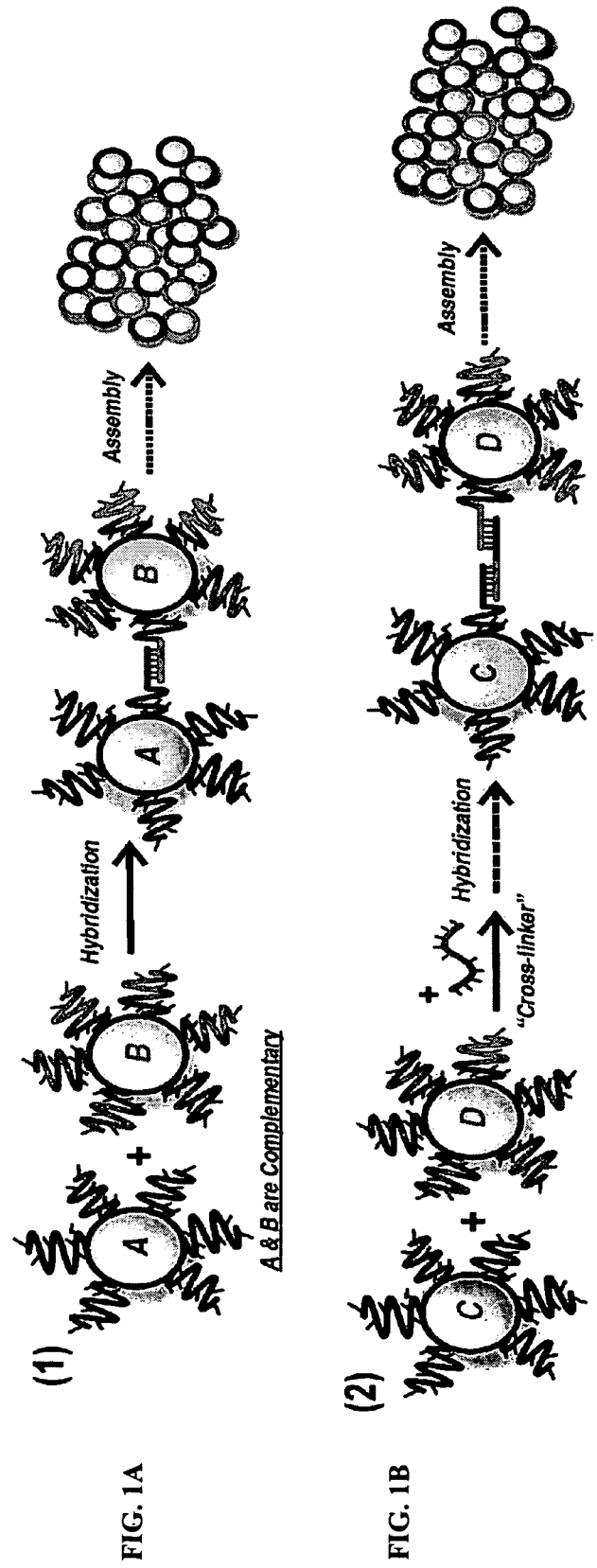
FIGS. 1A and 1B show cartoon depictions of DNA-mediated assembly of nanoparticles.

Self-assembly of nanoparticles into structures with long-range order hinges on control over the form of the interparticle potential and its range in respect to particle size, as well as over assembly kinetics. The use of DNA to mediate nanoparticle assembly may allow for the qualitative regulation of these parameters. The balance between the adhesive energy of DNA hybridization and the steric repulsion provided by interacting DNA strands may play a role in the formation of long-range ordering and a diversity of ordered phases. Experimental implementations of this approach have demonstrated the ability of single-stranded DNA (ssDNA) to provide a wide range of osmotic pressures between particles, which regulate the kinetics and offset of system assembly. Notwithstanding these calculations and studies, long-range ordering in DNA-mediated nanoparticle assemblies had yet to be observed.

Model systems of DNA-capped nanoparticles may be used to systematically explore the dependence between DNA structure, which regulates hybridization-induced attraction and osmotic repulsion, and the internal arrangement of the particles in DNA-mediated assemblies. A convenient way to monitor the structural evolution within such assemblies is to use in situ synchrotron small angle x-ray scattering (SAXS). The invention, in some aspects, identifies the DNA design and thermodynamical pathways necessary for the formation of well defined three-dimensional (3D) crystalline particle organization. In some embodiments such structures are formed.

As can be seen from FIGS. 1-5, DNA character and composition may be used to finely control the self-assembly kinetics, as well as final assembled aggregate size and morphology of nanoparticles. In one embodiment of the invention, a spacer sequence in the capping DNA is made "rigid" through hybridization with its complementary sequence in order to extend the aggregation-promoting complementary sequence away from the interface of the nanoparticles. In this embodiment of the invention, a spacer sequence is located near the particle-bound terminus of the capping DNA. When the spacer sequence is hybridized with its complement, the aggregation-promoting sequence of the capping DNA no longer interacts with the nanoparticle surface, thereby enhancing the hybridization and aggregation kinetics.

Another aspect of this embodiment relates to the use of the rigidification of the spacer sequence to control the inter-particle distance in the aggregated nanoparticles. By varying the length of the spacer sequence and its complement the inter-particle distance in the aggregates can be controlled.

In another embodiment of the invention, neutral, non-complementary DNA is included in the capping mixture. By changing the amount of neutral, non-complementary DNA relative to the aggregation-promoting complementary DNA, the sizes of the aggregates and the number of possible linkages per nanoparticle can be controlled. In this embodiment, the use of the rigidified spacer sequences provides additional enhancement of the aggregation kinetics. In some embodiments the rigidified spacer sequence comprises at least one segment of double-stranded DNA.

FIGS. 1A and 1B show cartoon depictions of prior art DNA-mediated assembly of nanoparticles. In (1A), the DNA sequences on nanoparticle A (2) and nanoparticle B (4) are complementary to each other, and particles self-assemble upon mixing. In FIG. 1B, the DNA on nanoparticles C (6) and D (8) are not complementary to one another, but are each complementary to separate portions of the cross-linker strand (13), which induces self-assembly. In scheme 1 (FIG. 1A), sets of nanoparticles are functionalized with complementary single stranded DNA. Upon mixing the two particles together, there is hybridization between the DNAs, and ultimately large scale aggregation. In scheme 2 of FIG. 1B, sets of nanoparticles are first functionalized with non-complementary sets of DNA. However, upon the addition of a single stranded piece of DNA (13), portions of which are complementary to each of the DNAs, cross-linking will occur, causing assembly. The strategy illustrated in scheme 2 is the more commonly used route due to its usefulness in biodiagnostics. In these cases, the cross-linker strand (13) is a target strand of unknown concentration or of unknown sequence. By adding nanoparticles that are functionalized with DNA, any aggregation induced by the cross-linker results in its detection. Detection is based on the optical properties of the gold nanoparticles themselves, which are a wine-red when soluble in solution, and darker red or purple when assembled.

In FIG. 1A, particles A (2) and B (4) have complementary recognition sequences (3) and non-complementary spacer regions (5). These sequences need not be the same on both particles and may include regions with different sequences of bases and in differing lengths. They hybridize to form a hybrid with spacers (14) and a linked region (10) formed by a linker (12), here provided by the linking of mutually complementary recognition sequences. On further incubation, the linked nanoparticles (NP) may form aggregates (16). FIG. 1B depicts a situation in which two particles, C (6) and D (8) are not mutually complementary. Again they are possessed of recognitions sequences (7) and spacer sequences (9). These sequences need not be the same on both particles and may include regions with different sequences of bases and in differing lengths. In this situation a linker (13) is required to link the two particles along a linking region (11). On hybridization the linker links the particles along the linking region (11) which is stood off from the uncapped NP by a spacer (15). Again, the linked NP may form aggregates (18).

A second novel property of using DNA-induced self-assembly, is the propensity for the DNA-linkages to melt at a temperature which is dependent upon the sequences of DNA used, the number of linkages between nanoparticles, and the local salt environment. This allows for additional biodiagnostics approaches to be developed based on assembly melting point, but also, the ability to simply disassemble nanoparticle assemblies. This disassembly is a remarkable property of these systems, and similar phenomena have not been shown in other systems. A third advantage of using DNA-induced self-assembly of nanoparticles is the unique property for DNA to form complex and extended structures. In this field, known as DNA-scaffolding, DNA addressability and programmability is utilized to form extended geometries and morphologies.

Despite these advances in using DNA to self-assemble nanoparticles, there are still many limitations and technical hurdles. A few of these limitations involve assembly-interfering coordination of the DNA to the nanoparticle interface. Because nanoparticle surfaces are highly reactive, and generally positively charged, the DNA adsorbs strongly to the surface. This causes the DNA sequences to become inaccessible for hybridization, resulting in poor nanoparticle assembly kinetics. This is especially true for systems that use low DNA coverage. One aspect of the present invention addresses this issue through extension of the aggregation-promoting complementary DNA sequences away from the nanoparticle interface.

While self-assembly is indeed induced by DNA-hybridization, difficulties in controlling and in optimizing the assembly kinetics and aggregate sizes are still limiting applications. Thus the ability to increase assembly kinetics may lead to lower detection times for bio-diagnostics, and the ability to control aggregate morphology without extensive purification steps based on size exclusion will aid in controlling aggregate morphology and spatial properties (interparticle distances), as well as aggregate melting properties. Thus another aspect of the present invention provides systems for enhanced kinetic control of aggregate formation.

In some embodiments, a plasmonic crystal is formed from a metamaterial comprising two or more types of particle, of the same or different materials, linked along a linking region by mutually complementary segments of DNA that cap the particles, and not linked along regions of neutral segments of the DNA.

In some variations, a plasmonic crystal is formed comprising a bio-inspired metamaterial displaying long-range three-dimensional crystalline order, the metamaterial comprising a plurality of nano-objects of types one and two, the nano-objects of type one functionalized with a first nucleic acid sequence comprising a linking region and a neutral region, wherein at least one segment of neutral region is double-stranded, the nano-objects of type two functionalized with a second nucleic acid sequence comprising a linking region and a neutral region, the functionalized nano-objects linked by hybridization of their respective linking regions, the linked nano-objects assembled into a non-close-packed crystal structure.

In some variations of the plasmonic crystal, the linking regions of the nano-objects of types one and two are non-interacting; the functionalized nano-objects are linked by hybridization of their respective linking regions with first and second recognition regions of a third nucleic acid sequence; the first recognition region complementary to the linking region of the nano-objects of type one; and the second recognition region complementary to the linking region of the nano-objects of type two.

In other variations of the plasmonic crystal, the first and second nucleic acid sequences comprise sequences of PNA. In other variations of the plasmonic crystal, the first and second nucleic acid sequences are chosen from the group consisting of sequences of DNA, sequences of RNA, and sequences of RNA and sequences of DNA.

In other variations of the plasmonic crystal, the metamaterial has a body-centered cubic crystal structure.

In other variations of the plasmonic crystal, the functionalized nano-objects comprise less than about 10% of the volume of the crystal.

Some embodiments of the metamaterials made by the methods described herein offer very open crystal structures, with the functionalized particles occupying less than about ten percent of the volume of the crystal. In some embodiments these open structures are used as catalysts or as substrates for catalysts.

In some embodiments, the catalyst comprises: a nanoparticle assembly including two types of nano-objects, each functionalized with a nucleic acid sequence containing a linking section and a neutral section, wherein at least one segment of neutral section is double-stranded; the assembly displaying long-range crystalline order; the long-range crystalline order comprising a crystal having a non-close-packed crystal structure; and the nanoparticle assembly operable to catalyze a chemical reaction.

In some variations of the catalyst, the functionalized nano-objects occupy less than ten percent of the total volume of the crystal. In other variations of the catalyst, the non-close-packed crystal structure is a body-centered cubic crystal structure.

In other variations of the catalyst, the nanoparticle assembly further comprises a third type of nano-object. In other variations of the catalyst, the third type of nano-object is functionalized with a sequence of non-interacting nucleic acid, wherein the concentration of the non-interacting nucleic acid sequence functionalizing the third type of nano-object is less than about 95%.

In other variations of the catalyst, wherein: the nucleic acid sequences are selected from the group consisting of sequences of PNA, sequences of DNA, sequences of RNA, and sequences of DNA and sequences of RNA. In other variations of the catalyst, a sequence of RNA is operable to catalyze a chemical reaction.

In other variations of the catalyst, the nanoparticle assembly further comprises an inorganic material adsorbed onto a surface of the nanoparticle assembly, the inorganic material operable to catalyze a chemical reaction.

EXAMPLES

Various types—metallic, semiconductive, magnetic, dielectric and their combination—and shapes—spherical, rod-shaped, icosahedral, planar, tubular, etc.—of particles may form part of, and can be used in the process of assembly of, 3D ordered structures. As used herein, unless otherwise noted, "particle" should be construed to include micro-objects (including microspheres, microrods, etc.) and nano-objects (fullerenes, quantum dots, nanorods, nanotubes, etc.). DNA of varied lengths can be attached to these particles via a number of functionalization routes, including: metal-DNA binding (via thiol- or amine-terminated DNAs chemisorption with unmodified Au, Ag, or Pt nanoparticles, etc.), organic cross-linking (via chemical coupling between amine-, thiol-, carboxylic acid-, etc., functionalized DNA and particles with carboxylic acid, amine, thiol, ketone, aldehyde, etc. surface functionalization), and bio-affinity (via specific biological interactions, protein-protein, DNA-protein, DNA-DNA, etc. between bio-functionalized DNA and biologically modified particles).

Furthermore, nucleic acid functionalization of micro- and nano-objects need not be limited to DNA functionalization. Ribonucleic acid (RNA) may be used rather than, or in conjunction with, DNA to take advantage of its unique properties. Similarly peptide nucleic acid (PNA) may be more stable than DNA, and so may find uses in environments too harsh for DNA-functionalized particles.

Here follow several concrete examples of DNA-guided particle assemblages and methods for making them. It should be understood that the examples are illustrative only and in no way limiting. For example, the DNA sequences used need not be those enumerated; any DNA sequences with the desired lengths of complementary and non-interacting segments may be employed. Furthermore, both A and B strands may be entirely non-interacting and may be hybridized and joined by a separate linking sequence. The lengths and/or ratios of lengths of spacer and linker regions may be varied from those described. The choice of particle material and size depends on the proposed application of the resulting metamaterial. Particles A and B, in particular, may be of different materials, e.g. gold and silver, and even of material types, e.g. gold and cadmium selenide. Three or more particle types may be assembled, for example gold-silver-platinum or iron-carbon-chromium-vanadium.

Example 1

Tunability of Assembly Kinetics

Nanoparticle Synthesis Gold nanoparticles (Au, 9.6±0.6 nm) were synthesized by a slightly modified citrate (Cit) reduction procedure. Briefly, an aged 1 mM HAuCl$_4$ solution was heated to ~95° C. for 30 minutes. To this solution a warm 38 mM trisodium citrate solution (10 ml) was added in one aliquot. Upon initial color change to red, the solution was then immediately cooled to ~80° C. and annealed for 2 hours. The sample was then allowed to cool naturally to room temperature with overnight stirring. The solution was then purified via centrifugation (30 min, 7,000 RPM) and stored at desired concentrations protected from light. In an exemplary experiment, the size of the Au particles increased with longer boiling times. The Au concentrations were calculated via measured extinction coefficients of $1.0 \times 10^8$ L mole$^{-1}$ cm$^{-1}$.

DNA-Nanoparticle Modification: Thiol-functionalized single stranded oligonucleotides of type 1 (1=5'-TAC TTC CAA TCC AAT-(T)$_{15}$-C$_3$H$_6$—SH— 3') (SEQ ID NO: 1) and type 2 (2=5'-ATT GGA TTG GAA GTA-(T)15-C3H6-SH— 3')(SEQ ID NO: 2), were purchased from IDT, Inc. as disulfides. In a typical experiment the samples were first reduced by dissolving the lyophilized samples (200-300 nmoles) with 0.3 ml of 100 mM dithiolthreitol (DTT) solution in purified water or buffer for 30 minutes. The samples were then loaded onto a freshly prepared cross-linked dextran gel (Sephadex®) column (G-25, Amersham Bioscience) and eluted with 2.5 ml 10 mM phosphate buffer (pH 7.0). The oligonucleotide concentration was quantified using UV-Vis analysis with the specific extinction coefficient. The 3'-thiol modification for type 1 and type 2 ssDNA were chosen as a model study, however 5'-thiol modifications can also be used. It was recently shown that 5'-thiol modification (HSC$_6$H$_{12}$-ssDNA) linker sequences allow for increased surface densities on gold nanoparticles using gel electrophoresis measurements when compared with 3'-thiol modification (HSC$_3$H$_6$-ssDNA). A 15-base (15b) poly-dT spacer was chosen due to its known low coordination to the gold interface to improve sample stability and coverage.

The synthesized Au particles were then functionalized with oligonucleotide 1 or 2, following methods for high DNA coverage. In a typical experiment an aliquot (1-50 μl) of a 50-300 μM solution of oligonucleotide was added to a purified water solution of Cit-Au ([Cit-Au]=10-30 nM). The ratio of oligonucleotide/Au was manipulated to control coverage of Au. In this experiment the ratio was kept at 300:1. The oligonucleotide+Au solution was allowed to incubate in an un-buffered solution for at least 12 hrs before being brought to a 10 mM phosphate buffer (pH 7.1) concentration and allowed to anneal for an additional ~4 hrs at room temperature. The salt concentration was then increased initially to 0.1 M NaCl for ~6 hrs, and finally to a 0.3 M NaCl concentration for an additional 12 hrs. The oligonucleotide-modified Au (1-Au, 2-Au) were stable indefinitely at these high salt concentrations. The solution was purified of excess DNA by centrifugations at 7,000 RPM for 30 minutes. The supernatant was collected and measured for excess DNA and the concentrated particles were re-dispersed in 0.3 MPBS. This cleaning process was typically repeated at least 3 times. The number (n) of type 1 or type 2 oligonucleotides bound to each Au at this feed ratio was calculated to be ~50 (~26.4 pmol/cm$^2$) by fluorescence and UV-Vis analysis.

Sample Preparation: In this study, the assembly between 1-Au and 2-Au (sys-VII of FIG. 2A) was carried out by combining equal volumes (200 μl) of 1-Au and 2-Au at equal concentrations ([Au]=4.5~7.5 nM) with mixing. In sys-VIII (FIG. 2B), the identical spacer segments of 1-Au and 2-Au precursors were first hybridized by a 15-base oligo-dA, at a molar ratio of 500:1 in 0.3 M PBS. This ratio is approximately a 10-fold excess of surface-bound 1 or 2 when n of ~50 per nanoparticle is taken into account. The samples were incubated overnight to form dsDNA spacer segments, resulting in 1*-Au and 2*-Au, and purified of excess oligo-da by multiple centrifugations and washing with buffer as above. It is currently undetermined how many of the available oligo-dT spacer sequences are hybridized by this excess concentration of oligo-dA. Recent thermodynamic investigations have shown unsaturated hybridization at nanoparticle surfaces is common. However, because the dynamic light scattering (DLS) measurements reveal DNA-capping thickness values that are close to the idealized model, it is likely that a large percentage of spacer sequences had been hybridized. For comparison purposes, the assembly for sys-VIII was always carried out with identical Au sizes, DNA coverage, solution conditions and concentrations, within usual laboratory error parameters.

Figures 2A, 2B:
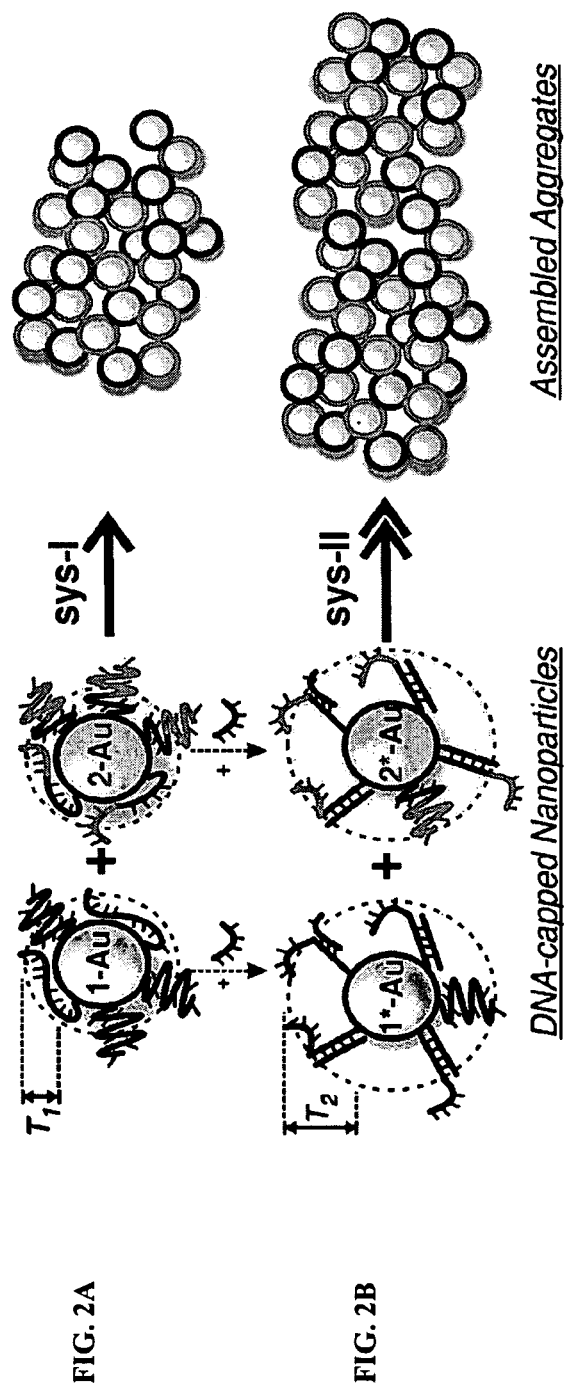
FIGS. 2A and 2B demonstrate an idealized representation for the DNA-induced self assembly of nanoparticles with complementary single-stranded (ss) DNA capping.

This example serves to demonstrate the tunability of assembly kinetics for DNA-capped nanoparticle systems achieved by tailoring the conformation of the surface bound DNA. The model systems used were gold nanoparticles (Au, 9.6±0.6 nm) complementary-capped with either single-stranded (ss) or partially rigid double-stranded (ds) spacer sequences, as illustrated in FIGS. 2A and 2B. The Au were capped with about 50 single strands of DNA 1(1=5'-TAC TTC CAA TCC AAT-(T)$_{15}$-C$_3$H$_6$—SH— 3')(SEQ ID NO: 3) or DNA 2 (2=5'-ATT GGA TTG GAA GTA-(T)$_{15}$-C$_3$H$_6$—SH— 3')(SEQ ID NO: 4), forming 1-Au (20) and 2-Au (22) respectively. In the first assembly system (sys-VII), only ssDNA capping was used (i.e., 1-Au+2-Au). In system 2 (sys-VIII), the same types of particles, 1-Au and 2-Au, were first hybridized at their oligo-dT spacer segment ((T)15) with a 15-base oligo-dA strand, forming the partially dsDNA capping of 1*-Au (24) and 2*-Au (26). This hybridization results in a conformational change from coiled ssDNA to partially rigid dsDNA, which results in extending the aggregation-promoting complementary sequences of the DNAs (1 and 2) away from the particle interface, helping to overcome the assembly-interfering effects of coiling and coordination to the Au interface. The aggregates (28, 30) formed by sys-VII and sys-VIII, respectively, may be of different or the same size. Particles 1-Au and 2-Au are functionalized with ssDNA only. The linking DNA (32) mutually hybridize, while the neutral DNA (36) do not participate in the hybridization. Particles 1*-Au (24) and 2*-Au (26) are functionalized with both neutral (non-complementary DNA strands which are unable to hybridize in the assembly process) ssDNA (38) which does not participate in hybridization, and partially hybridized DNA (40) which is partially rigid. The partially rigid functionalizing DNA (40) stands off the linking regions from the uncapped nano-object surface, resulting in a larger interparticle distance than for ssDNA.

The assembly in sys-VII and sys-VIII lead to the growth of large aggregates containing thousands of individual Au NPs. The melting properties of these aggregates were characterized, revealing melting temperatures ($T_m$) of ~59° C. and ~61° C. for sys-VII and sys-VIII respectively. These results provide evidence for the DNA-linkages between Au NPs, and suggest local differences between sys-VII and sys-VIII.

Figure 4:
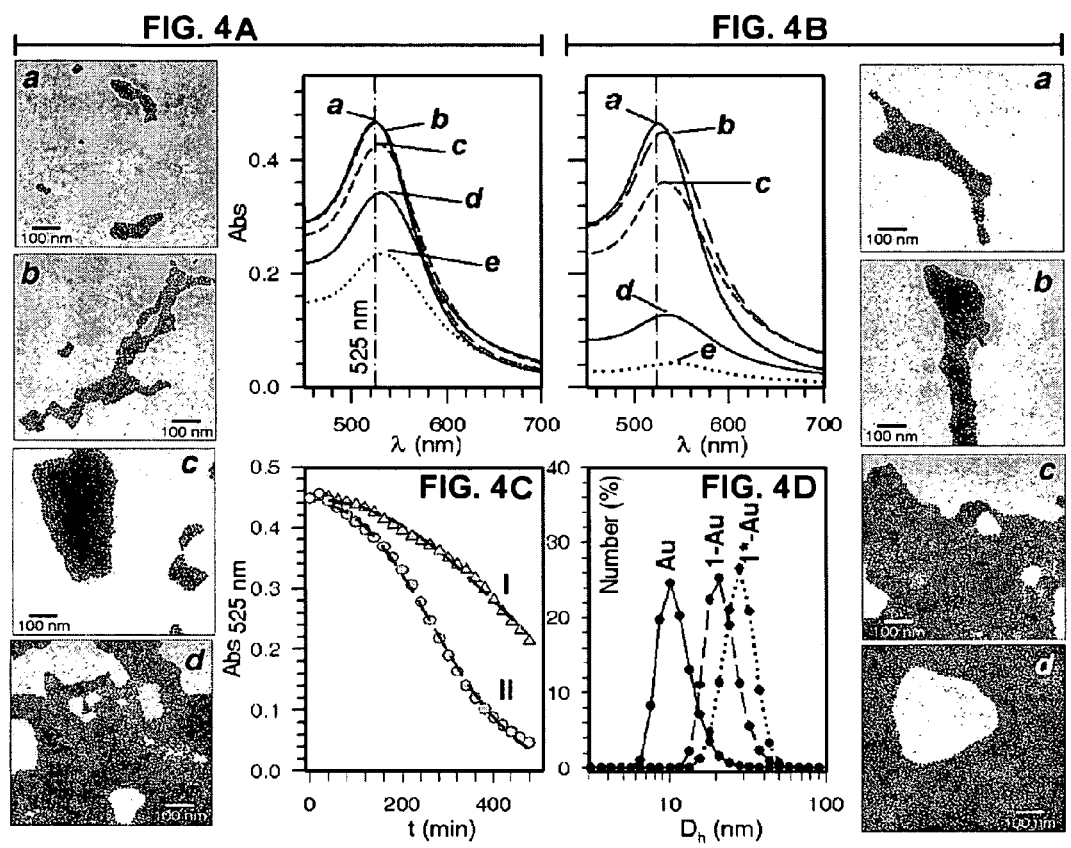
FIGS. 4A, 4B, 4C, and 4D represent the evolution of typical ultraviolet-visible spectrophotometry (UV-Vis), transmission electronic microscopy (TEM), and dynamic light scattering (DLS) results, and kinetic plots derived therefrom, from assemblages at different times.

To investigate these differences, we monitored the self-assembly process in situ with UV-Visible spectrophotometry (UV-Vis). UV-Vis probes the surface plasmon (SP) resonance band, which is associated with Au and assembled Au nanostructures, and is the basis for many colorimetric detection methods. FIG. 4 shows a set of UV-Vis data for sys-VII (A) and sys-VIII (B), measured during assembly under virtually identical conditions and concentrations. Assembly is apparent in the UV-Vis due to a red-shift in SP band position with band broadening (525-900 nm) and the decrease in extinction over time.

FIGS. 4A, 4B, 4C, and 4D represent the evolution of typical UV-Vis, TEM, and DLS results, and kinetic plots derived therefrom, from assemblages at different times. Representative UV-Vis and TEM results for the assembly in sys-VII (FIG. 4A) and sys-VIII (FIG. 4B) measured at 10 (a), 60 (b), 180 (c), 350 (d), and 485 (e) minutes. The aggregates (56) in FIG. 4A can be seen to be smaller at all time steps than those (58) in FIG. 4B. The particular solution used here was [1-Au]=[2-Au]=4.6 nM, [1*-Au]=[2*-Au]=4.6 nM, in 0.3 M NaCl, 10 mM phosphate buffer, pH 7.0 (hereinafter 0.3M PBS). The kinetic plots for sys-VII (VII) and sys-VIII (VIII) as monitored by UV-Vis at 525 nm with Avrami fitting are shown in FIG. 4C. DLS results for uncapped Au, 1-Au, and 1*-Au appear in FIG. 4D.

Recently, electrodynamics simulations of the optical properties for DNA-mediated assembly revealed major contributions to the extinction spectra from the screening of Au within the growing aggregate, an increasing scattering component over time, and the requirement that aggregates contain a few hundred individual Au to show changes similar to FIGS. 4A and 4B. In the experimental system, the aggregation is also followed by sedimentation at long assembly times. For sys-VII (FIG. 4A) the first hour of assembly reveals little observable change to the SP band (a-b). Over the course of about 8 hours the surface plasmon resonance band (SP band) undergoes a small red shift in wavelength from 525 nm to 533 nm, with a noticeable extinction decrease (c-e). These changes for sys-VII are the result of relatively inefficient hybridization between 1-Au and 2-Au and slow aggregate growth.

In contrast, FIG. 4B shows the enhanced UV-Vis progression for sys-VIII, which reveals two major differences from sys-VII. First, there is an immediate SP band red shift to about 535 nm (a), followed by a continued red shift and broadening after 1 hour (b). Secondly, the decrease in extinction at long reaction times proceeds at a much higher rate (c-e). These optical changes suggest both that the assembly kinetics are faster and that aggregate sizes are larger in sys-VIII than sys-VII.

To investigate aggregate size and morphology, transmission electron microscopy (TEM) results for samples from the corresponding UV-Vis spectra are also shown in FIGS. 4A and 4B. A trend of increasing aggregate size during assembly is clearly observed, with aggregates for sys-VIII showing larger morphologies for a given assembly time. To probe the structural details of these aggregates in their native buffer environments, we utilized in-situ small angle X-ray scattering (SAXS) with synchrotron radiation. SAXS results revealed interparticle distances for the assembled aggregates of 11~12 nm after annealing at 50° C., with sys-VIII consistently showing larger interparticle distances by 0.5~1.0 nm over sys-VII.

To further assess the assembly process in sys-VII and sys-VIII, kinetics were monitored by following the SP band at 525 nm (FIG. 4C). The kinetic plots describe a gradual decay in absorbance, which is more prominent for sys-VIII. The kinetic profiles for additional wavelengths reveal similar trends. To qualitatively contrast these kinetic profiles, we described them using Avrami law for nucleation and growth. Assuming that the SP band at 525 nm is mainly attributed to the individual particles and relatively small aggregates (a few hundred Au NPs), an expression of Avrami law can be parameterized for the UV-Vis monitoring as: $Abs=Abs_0 exp(-((t-t_0)/\tau)^n)$, where t is assembly time, $t_0$ is reaction onset time, $\tau$ is the characteristic time that depends on reaction rate and aggregate geometry, and n is the Avrami exponent that depends on the physical mechanism of aggregate growth. While this description does not separate various factors that influence extinction, as described above, it provides a reasonable description of the observed effects. By fitting the kinetic plots in FIG. 4C we determined $\tau$ of 568 and 328 min and n of 2.2 and 2.4 for sys-VII, and sys-VIII respectively. The decrease in $\tau$ for sys-VIII is indicative of an increased assembly rate, while the magnitude of n suggests a non-constant reaction rate, which can be attributed to diffusion limited growth and coalescence of the growing aggregates. The magnitude of $\tau$ was influenced by Au concentration as well as DNA surface density, however the trend in kinetics, sys-VIII>sys-VII, was always observed. It is interesting to note that when a system in which an equal mixture of ssDNA- and dsDNA-capping was used an intermediate $\tau$ of 492 min was observed.

The observed kinetic enhancement (~2x) may be attributed to the added rigidity of the DNA capping, which extends the aggregation-promoting complementary sequences away from the Au interface. To model this effect, the DNA-capping thickness (T) was estimated for the particles in each system (FIG. 2). The T for nanoparticles in sys-VII ($T_1$) was modeled as: $T_1 = T_1^C \sim 6$ nm, where $T_1^C$ is the end-to-end distance of a 30-base random coil oligonucleotide as described by the worm-like chain model. The T for nanoparticles in sys-VIII was modeled as: $T_2 = T_2^R + T_2^C \sim 9$ nm, where $T_2^R$ is the length of the rigid dsDNA 15-bp spacer segment, and $T_2^C$ is the end-to-end distance for the remaining 15-base oligonucleotide. From this approximation, we can expect a T increase of ~3 nm for isolated nanoparticles in sys-VIII vs. sys-VII.

To measure the actual changes in T DLS was utilized. FIG. 4D shows the DLS results for isolated uncapped-Au, 1-Au, and 1*-Au, which revealed hydrodynamic diameter values ($D_h$) of ~10.1, ~21.0, and ~28.1 nm respectively. These values correspond to a T of ~5.5 nm and ~9.0 nm for sys-VII and sys-VIII, respectively. This ~3.5-nm increase in T for the isolated nanoparticles is close to the estimated difference, and taken with the SAXS results showing an increased interparticle distance in sys-VIII for the assembled aggregates, reinforcing the conclusion that the extension of hybridizing sequences from the interface is responsible for more favorable assembly conditions.

Increasing the rigidity of the DNA-capping structure allowed for the extension of the aggregation-promoting complementary sequences away from the nanoparticle interface, which facilitated enhanced assembly kinetics and provided a means of increasing the interparticle distances in the assembled aggregates. This approach can be generalized for more sophisticated DNA-capped systems, which may have potential use in nano-construction by design.

Calculations: To estimate the thickness (T) of the DNA capping at the nanoparticle interfaces we estimated the mean square end-to-end distances ($<R^2>$) of the DNA. For the ssDNA-capping case, the thickness (T), was estimated by $T_1 = T_1^C \sim 6$ nm, where $T_1^C$ was estimated by the $(<R^2>)^{0.05}$ of:

$$<R^2> = 2PL\left(1 - \frac{P}{L}(1 - e^{-L/P})\right),$$

where P is the persistence length (~1 nm) and L is the contour length (~0.65 nm/base) for the ssDNA case (sys-VII). For the dsDNA-capping case (sys-VIII), $T_2 = T_2^R + T_2^C \sim 9$ nm, $T_2^R$ was the estimated length of a 15-bp double helix (0.34 nm/base), and the additional 15 base $T_2^C$, was calculated as above. In these idealized estimations no account was taken of chain-chain or chain-surface interactions, as the proper quantitative implementation of these effects is rather difficult for the system. However, such interactions will only change absolute values of DNA capping thickness and should not affect the overall conclusion that $T_2$ is larger than $T_1$. Besides physical extension of the linker segments away from the Au interface, and reduced coordination to gold surface, such a change may open up a number of void spaces in the DNA capping, which may promote hybridization.

Kinetic Model Quantifying the difference in assembly kinetics among the studied systems may be described by kinetic plots using the Avrami law for nucleation growth. In this description, the isotropic growth of the DNA functionalized nanoparticle aggregate is an isothermal reaction that leads to the formation of a newly transformed phase with a volume fraction $\chi = 1 - exp(-((t-t_0)/\tau)^n)$, where t is time, $t_0$ is reaction onset time, $\tau$ is the characteristic time that depends on reaction rate and aggregate geometry, and n is the Avrami exponent that depends on the physical mechanism of aggregate growth. Thus, assuming that the extinction at 525 µm can be mainly attributed to the individual particles and relatively small particle clusters (less than a few hundred Au particles), and the proportionality between absorbance A and particles or small clusters of concentration C, the kinetics plot can be parameterized as $A = A_0 exp(-((t-t_0)/\tau)^n)$, where $A_0$ is directly related to C. While this parameterization does not separate various factors that influence extinction, as described above, it provides a reasonable description of the observed effects.

Instrumentation: Measurements in this example were carried out using the following instrumentation. This detail is provided for the clarity offered by using concrete examples rather than for endorsing any particular manufacturer; any instrumentation of similar capability may be used.

UV-Visible Spectrophotometry (UV-Vis): UV-Vis spectra were collected on a Perkin-Elmer Lambda 35 spectrometer (200-900 nm). Melting analysis was performed in conjunction with a Perkin-Elmer PTP-1 Peltier Temperature Programmer and was performed between 20° C. and 75° C. with a temperature ramp of 1° C./min while stirring.

Transmission Electron Microscopy (TEM): TEM images were collected on a JEOL-1300 microscope operated at 120 kV. The samples were prepared by drop casting an aqueous nanoparticle or assembly solution onto a carbon coated copper grid, followed by the slow removal of excess solution with filter paper after 5 minutes.

High Resolution Transmission Electron Microscopy (HR-TEM): HRTEM images were collected on a JEOL-4000 EX microscope operated at 400 kV at the Brookhaven National Laboratory Center for Functional Nanomaterials Electron Microscopy Facility. The samples were prepared by dropcasting an aqueous solution on a carbon coated copper grid, followed by the slow removal of excess solution with filter paper after 5 minutes.

Dynamic Light Scattering (DLS): The DLS results were measured using a Malvern Zetasizer ZS instrument. The instrument is equipped with a 633 nm laser source, and a backscattering detector at 173°. Data was analyzed using CONTIN method.

Small Angle X-ray Scattering (SAXS): The in-situ SAXS experiments were performed at the National Synchrotron Light Source (NSLS) X-22B beamline. The scattering data was collected with a CCD area detector, and 1D profiles of scattering are presented as intensity vs. scattering vector, $q=[(4\pi n/\lambda_0)/\sin(\theta/2)]$, where n is the refractive index of the medium, $\lambda_0$ the wavelength of incident X-ray, and $\theta$ the scattering angle, respectively. Interparticle spacing, d, was calculated by, $d=2\pi/q$. The values of q were calibrated versus silver behenate ($q=0.1076$ $A^{-1}$). SAXS results were collected for DNA-mediated assembly samples after full precipitation and dispersion in 0.3 M PBS buffer solution, following by annealing at 50° C. to yield thermodynamically stable aggregates. Samples were contained in quartz capillary in a holder under temperature control.

The ability to control interparticle distance and the number of linkages between nanoparticles is also currently limited. Control of these features will define optical and electronic properties of novel materials based on nanoparticle assemblies. Another aspect of the present invention provides systems for controlling interparticle spacing and methods for varying the number of linkages to each nanoparticle.

To overcome problems of single stranded DNA coordination to the surface, we make use of double stranded DNA regions of the surface bound DNA, which do not participate directly in the assembly. This extends the aggregation-promoting complementary DNA sequences, away from the nanoparticle interface, thus increasing the accessibility for DNA hybridization (Scheme 2 of FIG. 2B). FIGS. 2A and 2B demonstrate an idealized representation for the DNA-induced self assembly of nanoparticles. FIG. 2A (Sys-VII) depicts an idealized representation for the DNA-induced self assembly of nanoparticles with complementary single strand (ss) DNA-capping. Sys-VIII, shown in FIG. 2B, represents the same type of ssDNA-capped nanoparticles after hybridization of the spacer sequences of the DNA strands, which extends the aggregation-promoting complementary DNA sequences away from the nanoparticle interface.

To better control assembly kinetics and aggregate sizes one can use a combination of complementary DNA strands (using complementary DNA to drive the hybridization-based assembly process between particles) and neutral DNA strands to fine tune affinity between particles. In addition, the spacer regions of these DNA molecules were rendered double stranded, to extend the DNA away from the surface of the nanoparticles, making the hybridizing DNA more accessible as part of the assembly process. For similar reasons, we also present the use of double stranded spacer sequences in the neutral DNA (Scheme 3, FIG. 3). The use of double stranded spacer sequences and single stranded regions for hybridization-driven assembly also permits better control of interparticle distances.

FIGS. 3A, 3B, and 3C depict an idealized illustration for the assembly between nanoparticles with both complementary and non-complementary ssDNA-capping before and after hybridization. An idealized illustration for the assembly between nanoparticles both complementary and non-complementary ssDNA-capping (A:C, and A':C) where A (44) and A' (46) are complementary aggregation-promoting sequences and C (52) represents a "neutral" unrelated (non-complementary) sequence appears in FIG. 3A. The ratio between complementary and neutral capping sequences can be controlled in this system. FIG. 3B shows a virtually identical assembly system after the spacer sequences of the aggregation-promoting complementary strands are selectively hybridized to form rigid segments (denoted *A:C and *A':C), where *A (48) and *A'(50) are partially rigid. A similar nanoparticle system after the spacer sequences of the complementary and neutral strands have been hybridized (denoted *A:*C, and *A':*C), where *C (54) is now also partially rigid, is shown in FIG. 3C.

Example 2

Enhancement of Assembly Kinetics

The assembly kinetics was even more dramatically enhanced when the nanoparticle was functionalized with more than one type of ssDNA. FIG. 3 shows an idealized representation for a system which possesses both a complementary type 1 (A, A', *A, and *A') ssDNA, with the addition of a neutral, non-hybridizing strand of type 3 (C and *C) (3=5'-TTC TCT ACA CTG TCT-$(T)_{15}$-$C_3H_6$—SH—3')(SEQ ID NO: 5). The ratio between type 1 (or type 2) and type 3 can be controlled via functionalization methods.

FIG. 5A shows a set of kinetic plots for a system which consists of ~75% of non-complementary neutral type 3 (C) ssDNA and 25% complementary strands (A, A'), type 1 and type 2. Due to the presence of type 3 ssDNA, the assembly was extremely slow (circles). However, upon the selective hybridization of the spacer sequences of the aggregation-promoting complementary type 1 (*A) and type 2 (A') ssDNAs, the assembly kinetics were dramatically increased (triangles). FIG. 5B shows a virtually identical system measured with DLS, which shows the dramatic change in assembled aggregate size due to the addition of oligo-dA to rigidify the spacer sequence. Similar results were obtained for systems with 0-95% of type 3 non-complementary, neutral ssDNA. This method also allows control of assembled aggregate size. FIG. 5C shows the final assembly size for a system that contains 95% non-complementary neutral DNA. Each aggregate (60) contains only a few (1-4) nanoparticles. FIG. 5D shows a TEM image for a similar system which contained 85% neutral DNA, which reveals that each aggregate (62) contains ~5-15 nanoparticles.

FIGS. 5A, 5B, 5C, and 5D depict kinetic profiles, DLS results, and TEM images of assemblages comprising 85% and 95% neutral DNA. FIG. 5A shows kinetic profiles as measured by UV-Vis showing the dramatically enhanced assembly after addition of oligo-dA (triangles). In FIG. 5B, DLS results for a virtually identical sample showing the dramatic increase in aggregate size upon addition of oligo-dA (triangles). FIG. 5C presents a TEM image for the assembly for a system which possessed 95% non-complementary DNA. The TEM image (FIG. 5D) for the assembly for a system which possessed 85% non-complementary DNA can be compared to that of FIG. 5C, demonstrating again the increased aggregate size for the lower fraction of neutral DNA.

These results demonstrate that because DNA is extremely versatile, and because different regions of the ssDNA can be selectively hybridized, this type of system is an ideal candidate for future development of extremely precise and predictable nanoparticle self-assembly. An advantage of the inventive technology is the demonstration that simple partial hybridization of the DNA-capping allows for increased assembly kinetics. In addition, the use of neutral, non-complementary DNA can be used for controlling aggregate sizes and the numbers of linkages between nanoparticles.

Example 3

Crystalline Gold Nanoparticle Assemblages

Nanoparticle Synthesis & DNA-functionalization: Gold nanoparticles (Au, 11.4±1.0 nm) were synthesized by first heating a mM HAuCl$_4$ solution to ~95° C. for 30 minutes. To this solution, a warm (~40° C.) 10-ml aliquot of 38-mM trisodium citrate solution was added and let to react for a few minutes. Upon initial color change to red, the solution was immediately cooled to about 80° C. and annealed for 2 hours. The sample was left to cool to room temperature and allowed to stand overnight. The solution was then purified via centrifugation (30 min, 4,500 g) and stored at the desired concentrations in the dark.

Thiol- or amine-modified single-stranded oligonucleotides were purchased (Integrated DNA Technologies Inc., Coralville, Iowa, U.S.A; Primesyn Lab Inc., Hillsborough, N.J., U.S.A) as disulfides, Table 1. Before nanoparticle functionalization, the oligonucleotides were first reduced by dissolving the lyophilized samples (100-300 nmoles) for 30 minutes with 0.3 ml of a 100-mM dithiolthreitol (DTT) solution in purified water or buffer. The reduced DNA was loaded onto a freshly purified cross-linked dextran gel column (G-25, Amersham Bioscience) and eluted with 2.5 ml 10 mM phosphate buffer (pH=7.0). The DNA was quantified using UV-Vis analysis with the specific DNA extinction coefficient.

The synthesized Au NPs were then functionalized with DNA of lengths of 30-200 bases. In a typical experiment, an aliquot (1-50 µl) of a purified DNA 50-300 µM solution was added to a 1 ml solution of Au ([Au]=10-30 nM). The ssDNA+Au solutions were incubated at room temperature in a non buffered solution for at least 3 hours before adding phosphate buffer to bring its concentration to 10 mM (pH=7.1). The solution was left to anneal at 25° C. for 4 hours before the addition of NaCl (0.025 M). The salt concentration was then increased gradually from 0.025 to 0.3 M NaCl over 24 hours, and then left for an additional 24 hours at 0.3 M. The excess DNA next was removed from the solutions by centrifugation for 30 minutes at 4,500 g. This purification process was repeated three times. Fluorescence and Uv-Vis analyses showed that the total number (n) of ssDNA bound to each particle was ~60 (±5) (~31.7 µmol/cm$^2$).

SAXS Sample Preparation: Samples consisting of DNA-mediated assembled aggregates were prepared following methods described in the literature. In each system, assembly was carried out at 25° C. by combining equimolar amounts of type A and type B DNA-capped Au in 200 µL ([A]=[B]=~30 nM) solution of 10 mM phosphate buffer, 0.2 M NaCl, pH=7.1. Aggregates were allowed to assemble overnight, and the resulting precipitate were collected and transferred in buffer to quartz capillaries approximately 1.0 mm in diameter. The capillaries were sealed with wax to prevent evaporation.

Small Angle X-ray Scattering (SAXS): SAXS experiments were performed in situ at the National Synchrotron Light Source's (NSLS) X-21 beamline. The scattering data were collected with a MAR CCD area detector measuring one-dimensional (1D) scattering intensity vs. scattering vector, $q=(4\pi/\lambda)\sin(\theta/2)$, where $\lambda=1.5498$ Å is the wavelength of the incident X-rays, and $\theta$ is the scattering angle. The data are presented as the structure factor S(q) vs. q. The values of q were calibrated with silver behenate ($q=0.1076$ Å$^{-1}$) standards. S(q) was calculated as $I_a(q)/I_p(q)$, where $I_a(q)$ and $I_p(q)$ are background-corrected 1D scattering intensities extracted by angular averaging of CCD images for a system under consideration and unaggregated Au, respectively. The peak positions in S(q) are determined by fitting a Lorenzian form to the data.

UV-Vis: UV-Vis spectra were collected on a Perkin-Elmer Lambda 35 spectrometer (200-1100 nm). Melting analysis was performed in conjunction with a Perkin-Elmer PTP-1 Peltier Temperature Programmer between 20° C. and 75° C. with a temperature ramp of 1° C./min while stirring, in a 10 mM phosphate buffer, 0.20 M NaCl, pH=7.1, buffer solution.

FIG. 6 shows a schematic illustration of an approach wherein the interactions between DNA-capped 11.4 nm gold nanoparticles may be tailored by the structure of the attached DNA, as seen in systems I-VI. The assembled systems may be prepared by combining sets of nanoparticles with complementary DNA capping (denoted as particles A and B). The DNA in the capping possesses outer recognition sequences which participate in A-B hybridization, and interior spacer sequences which do not participate in the hybridization. In these systems, the length of the recognition sequence sets the scale of adhesion between particles, while the length of the flexible or rigid spacer defines the strength and range of repulsive interactions. Such repulsion originates via entropic interactions of hybridized strands, and strands that cannot hybridize due to geometrical constraints. By modifying independently the length of either the recognition or spacer segments in the DNA capping, the overall interparticle interaction may be varied. Specific examples of some embodiments of the invention follow.

Six exemplary functionalized nanoparticle systems, systems I-VI, were produced by the same methods. The hybridization-induced assembly of equimolar amounts of A (a first type of particle, 104) and B (a second type of particle, 106) in systems I-V resulted in micrometer-sized aggregates, which were collected after incubation for 24 hours at 25° C. System VI (102) was prepared by hybridizing the spacer regions of system IV. The nanoscale structure of these aggregates was then studied in situ by SAXS ($\lambda=1.5498$ Å) under temperature control with ±0.1° C. stability. FIG. 7 shows a representative set of SAXS images obtained for the aggregates from systems I-VI at ~28° C. and upon heating the aggregates to a pre-melting temperature ($T_{pm}$), which is a few degrees below the assemblage melting temperature ($T_m$). FIG. 8 shows the corresponding structure factors, S(q), which reveal the position of the first scattering peak. This peak position, $q_1$, corresponds to the shortest correlation length between particles, $d=2\pi/q_1$. For systems I (92), II (94), V (100), and VI (102), the observed spacings at ~28° C. ($d_I=15.6$, $d_{II}=19.4$, $d_V=17.9$, $d_{VI}=27.8$ nm) are shorter than in an ideal system estimated by the worm-like chain model for the end-to-end distances of the interparticle DNA linkages. System III (96) revealed a d which is ~1 nm larger than its model d, while system IV (98), having d of ~23.5 nm, resulted in the closest agreement with the model. Non-uniaxial hybridization of DNA and local hybridization defects may be responsible for such variability in d compared to the idealized case, resulting in particles being arrested in non-equilibrium states at room temperature after initial assembly. In such cases annealing can be advantageous in bringing the system to thermodynamic equilibrium.

FIG. 7 shows scattering patterns for the samples in as-assembled (114, T~room temperature) and pre-melting (T=$T_{pm}$) condition (118), at. At these temperatures, the interparticle adhesive energy is decreased, which permits local DNA and particle rearrangements. In each system, a shift was observed in the S(q) peak to lower q values (FIG. 8), indicating a d increase, which can be attributed to the development of more uniaxial character of hybridization with annealing, as well as to the conformational changes of DNA with increased temperature. For example, system IV showed a q-shift of ~0.005 $A^{-1}$, which corresponds to about a 20% (~4.5 nm) increase in particle surface-to-surface distance. In addition, SAXS measurements at $T_{pm}$ revealed a narrowing of the scattering peak for all systems, which is attributed to improved ordering. Compared to room temperature, at $T_{pm}$ systems I, II, III, and V show a 10-20% increase of scattering correlation length, $\xi \approx 2\pi/\Delta q$, where $\Delta q$ is resolution-corrected FWHM of the diffraction peak ($\Delta q_{res} \approx 0.0015$ $A^{-1}$), and $\xi$ is limited to only a few interparticle spacings. In contrast, systems IV and VI showed a more than 50% $\xi$ increase, to about 5d, accompanied by the emergence of higher order peaks. These reorganizations with temperature indicate that the particles in the aggregate are initially captured in metastable states. Upon annealing at $T_{pm}$, local rearrangement of the DNA linkages may take place, leading to particle position and orientation readjustments that optimize interparticle interactions by maximizing the number of DNA linkages between the particles. A component of this effect is the spacer structure, which allows for larger local rearrangements, due to the greater flexibility of the linkages and the smaller energies required for particle repositioning or rotation.

The disassembling of DNA-linked particle systems occurs with further temperature increase due to DNA dehybridization at $T_m$. This event is manifested by the disappearance of the scattering peaks shown in FIG. 8, and the emergence of only diffuse scattering, which is a signature of the form factor of individual nanoparticles rather than an assemblage. Systems II, III, and IV revealed structure disassembly within a few minutes, while systems I and VI showed broad residual peaks due to much slower kinetics. In system V, the 30-base (30-b) recognition segment hybridization resulted in a $T_m > 85°$ C. Upon cooling below $T_m$, each sample was found to reassemble into structures identical to their pre-melting state, except for system IV, which revealed an exceptionally sharp ring pattern suggesting spontaneous crystal formation. Low-temperature spectra (114) are shown by the darker lines and higher-temperature spectra (12) by the lighter lines.

Figure 9:
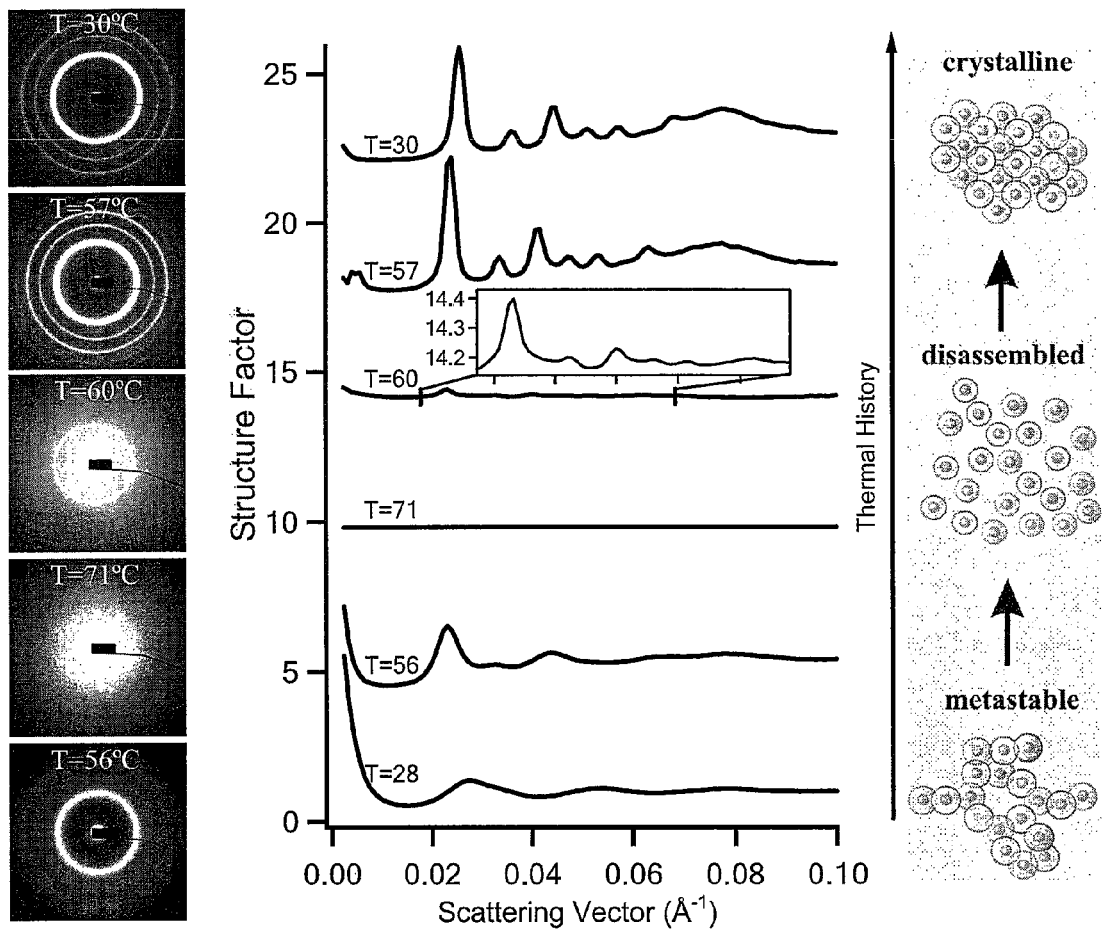
FIG. 9 shows SAXS images and extracted structure factors S(q) for system IV with a schematic illustrating its structural changes through the heating-cooling cycle across the assemblage melting point.

The experimental path towards ordering in system IV is illustrated in FIG. 9 which shows the scattering patterns and respective S(q) for the system in its annealed state before melting (56° C.), melted (71° C.), intermediate (60° C.), and ordered state after reassembly (57° C., 30° C.). This is illustrated in FIG. 9 by the metastable state (132), the disassembled state (134), above the dsDNA melting point, and the crystalline state (136) on cooling below the melting point. The evidence of ordered structure starts to appear immediately below $T_m$ at ~60° C., where S(q) reveals several diffraction peaks in the presence of strong diffuse scattering attributed to a large contribution by the nanoparticles' form factor. This suggests the presence of nuclei of the newly forming phase in coexistence with unassembled particles. Upon further cooling, to 59° C.-57° C., crystallization of the sample, as evidenced by the dramatic reduction of particle form factor contribution to the scattering and emergence of sharp circular patterns characteristic of un-oriented polycrystalline samples, i.e., powder scattering, is observed. This crystalline formation occurs within only a few minutes, unaffected by a cooling rate up to 1° C./min.

Figure 10:
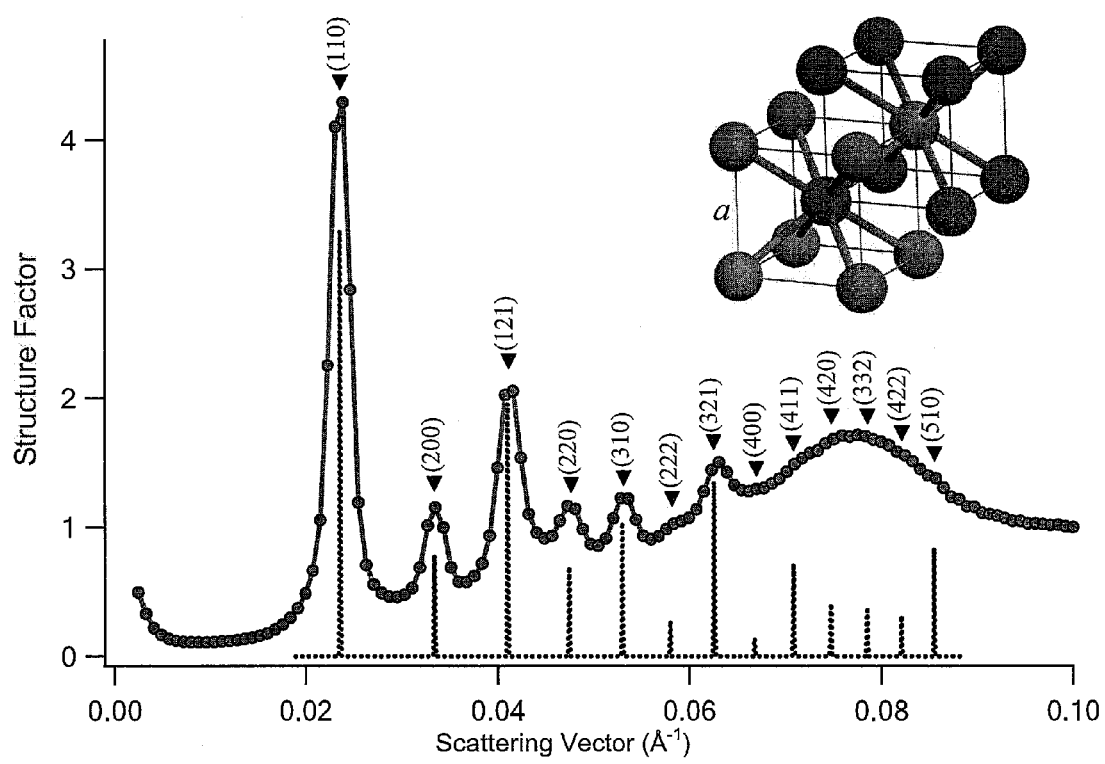
FIG. 10 shows the structure determination of the crystallized system IV.

The SAXS pattern in FIG. 9 reveals seven orders of resolution-limited Bragg's peaks, demonstrating the crystalline 3D structure of system IV, with a remarkable degree of long-range ordering, with $\epsilon$ larger than several hundred nanometers. Once formed, the development of the crystalline structure is reversible without a noticeable loss of ordering quality or changes in system behavior over multiple assembly-disassembly cycles. In addition, the crystalline structure was stable in solution over several days of SAXS monitoring. Analysis of the peak position ratios reveal $q_x/q_1=\sqrt{1}:\sqrt{2}:\sqrt{3}:\sqrt{4}:\sqrt{5}:\sqrt{6}:\sqrt{7}$, which correspond to Im'3m space group, a body-centered cubic (bcc) structure, as shown in FIG. 10. The peak height in S(q) also qualitatively follows the relative intensities predicted for a bcc arrangement. The corresponding lattice parameters (a) for the structure are ~37.5 nm at 57° C. and ~34.8 nm after cooling to 30° C., which corresponds to 21.1- and 18.7-nm surface-to-surface distances between cores of the particles in the first coordination shell. This structure is quite open, with nanoparticles occupying only ~3-4% of the structure volume, and DNA taking another 4-5%. Thus, more than ~90% of the assembled structure volume is occupied by solvent molecules, which is far higher than the typical void space of about 32% in packed hard spheres in a bcc orientation.

The crystal structure of the assemblages was unexpected, since the bcc structure formation is not commonly observed for hard sphere packing, which tends to form hexagonal close packed (hcp) or face-centered cubic (fcc) phases. It should be noted that, although both hcp and fcc structures are referred to as "close-packed" and the bcc structure as "non-close-packed," functionalized particles do not typically pack as closely as idealized hard spheres. The bcc structure accommodates well the requirement for optimizing interaction energies in the exemplary binary A-B system, with A-A and B-B interactions being mainly repulsive, by having only particle B in the coordination shell of A and vice versa. Nevertheless, a variety of crystal structures may be formed by altering the processing conditions or the structure of the DNA functionalizing the particles.

Varying the length and flexibility of the spacer in the systems I-VI permitted the determination of the conditions for formation of the assembled bcc crystalline phase, demonstrating that for a given recognition sequence length, longer and more flexible spacer sequences favor the formation of the assembled crystalline phases. These structural changes in DNA sequences can be correlated with a favorable interparticle interaction potential for long-range ordering. In particular, the length of the spacer segment in the DNA at least partially determines the range of interactions in relation to the particle size, and is on the order of particle size for the longest spacers studied in this exemplary experiment. DNA-induced crystallization may require long-range interactions, on the order of a particle size or larger, for achieving diversity in crystalline phases, with bcc phases being the most abundant. The softness of this potential, determined by the spacer length and flexibility, allows for a lower energy penalty for equal spatial displacement of particles. The complexity of DNA-mediated interactions, their discrete base-pair and strand character, as well as crowding effects, renders the quantitative determination of the potential's softness challenging, but empirical delineation of a set of conditions for spontaneous bcc crystalline formation is an important step towards the long-sought programmed ordering of nanoparticle assemblies. This approach to generating well-ordered metamaterials may lead to a rich diversity of phases unique to different assembly conditions and materials. This diversity may be achieved, for example, by altering the length of the spacer and recognition segments of the DNA sequences or by changing the ratio of their lengths, among other modifications.

Long-range order in an assemblage of DNA-capped gold nanoparticles may be achieved by varying interparticle interactions through the modification of DNA design. The correlation between lengths and rigidity of DNA segments, and the internal structure of assemblies may be investigated in situ using SAXS. A bcc crystalline structure of the DNA-capped nanoparticles created using the techniques described herein exhibits a correlation length of over hundreds of nanometers, and is remarkably open, with particles occupying only ~4% of the lattice volume. This crystalline organization of nanoparticles is thermodynamically stable and reversible, demonstrating a nearly 10% expansion of lattice constant over an approximately 30° C. range of temperatures. The example process demonstrates the ability to induce long-range order in nanoparticle assemblies via DNA. The long-range order persists over at least ten interparticle distances or unit cells. This suggests new pathways for creation of 3D crystalline structures from nanoscale objects with bio-recognition interactions. Such pathways may produce a diversity of phases in these systems, possibly leading to the next generation of metamaterials by design. The open structure, with concomitantly increased surface area, may be used to advantage in catalysis, either by acting as or by hosting a catalyst capable of accelerating a chemical reaction.

FIG. 6 depicts typical structures of DNA linkages, while FIG. 7 shows small-angle X-ray scattering (SAXS) results for unannealed and annealed DNA-linked nanoparticle aggregates having corresponding linkage structures. In FIG. 6's schematic, recognition (complementary) sequences are shown on the bottom of the linkage for DNA-capped particles A and on the top of the linkage for capped particles B. (For clarity, only one interparticle linkage is shown.) In the examples recited above, the nanoparticles of system I are functionalized with sequences of single-stranded DNA (ssDNA) each having a 3-b non-interacting neutral region and a 15-b complementary linking region along which particles A hybridize with particles B forming a 15-base pair (bp) double-stranded linked region. In system II, both particles have 15-b neutral regions and 15-b linking regions, and form a 15-bp linked region when hybridized. System III is asymmetric, with particles A having a 35-b spacer and a 15-b linker, while particles B have spacer segments and linker segments of 15 bases each. In system IV both A and B particles are functionalized with 35-b spacer (neutral) segments and 15-b linker (complementary) segments. The functionalized particles of system V have DNA sequences with 3-b spacers and 30-b linkers, while in system VI the spacers are double-stranded, consisting of 35 base pairs, and the linkers comprise 15 bases of ssDNA. The functionalized particles of system VI are obtained by hybridizing the spacer segments of system IV particles.

SAXS patterns for unannealed systems and systems annealed at the pre-melting temperature, $T_{pm}$, with the experimental temperature indicated on each image, appear in FIG. 7. The left-hand series shows results for unannealed systems, while the right-hand series corresponds to annealed samples. Scattering patterns for unannealed systems I-V were obtained at 28° C. and for unannealed system VI at 30° C. Data for the annealed samples were taken at 59° C. for system I, 57° C. for system II, 53° C. for system III, 56° C. for system IV, 71° C. for system V, and 62° C. for system VI.

FIG. 8 shows the extracted structure factors S(q) for scattering patterns shown in FIG. 7. The darker lines show S(q) for systems before annealing, while the lighter lines show S(q) for the systems as annealed. Positions of the first S(q) peaks for systems I through VI, respectively, are $q_I$=0.0403, $q_{II}$=0.0324, $q_{III}$=0.0273, $q_{IV}$=0.0266 $q_V$=0.0351, and $q_{VI}$=0.0226 Å$^{-1}$ at low temperature and $q_I$=0.037, $q_{II}$=0.0298, $q_{III}$=0.0244, $q_{IV}$=0.0233, $q_V$=0.029, and $q_{VI}$=0.0199 Å$^{-1}$ at $T_{pm}$. In FIG. 8, lighter lines refer to the annealed samples and the darker lines to the unannealed samples.

FIG. 9 shows SAXS images, extracted structure factors S(q), and schematics of the crystallization pathway for system IV. The unannealed system of nanoparticles is metastable. As the temperature is raised, the system melts and disassembles. Crystallization occurs on cooling, and is reproducible and stable through subsequent heating/cooling cycles across the assemblage melting temperature. S(q) lines are shifted consecutively by 4.4 units. The insert shows a magnified region of S(q) at 60° C. for the q range from 0.018 to 0.068 Å$^{-1}$.

TABLE 1

The ssDNA used in the study

| DNA Sequence (5' to 3') | SEQ ID NO |
|---|---|
| System-I | |
| A    TAC TTC CAA TCC AAT TTT-C$_6$H$_{12}$-SH | 6 |
| B    ATT GGA TTG GAA GTA TTT-C$_6$H$_{12}$-SH | 7 |
| System-II | |
| A    TAC TTC CAA TCC AAT TTT TTT TTT TTT-C$_3$H$_6$-SH | 8 |
| B    ATT GGA TTG GAA GTA TTT TTT TTT TTT-C$_3$H$_6$-SH | 9 |
| System-III | |
| A    TAC TTC CAA TCC AAT TCT TGT GTC GAT AGG TCG GTT GCT TTT TTT TTT TT-C$_6$H$_{12}$-SH | 10 |
| B    ATT GGA TTG GAA GTA TTT TTT TTT TTT-C$_3$H$_6$-SH | 11 |
| System-IV | |
| A    TAC TTC CAA TCC AAT TCT TGT GTC GAT AGG TCG GTT GCT TTT TTT TTT TT-C$_6$H$_{12}$-SH | 12 |
| B    ATT GGA TTG GAA GTA TCT TGT GTC GAT AGG TCG GTT GCT TTT TTT TTT TT-C$_6$H$_{12}$-SH | 13 |
| System-V | |
| A    TAC TTC CAA TCC AAT GAT ACG ACA CAG ATA TTT-C$_6$H$_{12}$-SH | 14 |
| B    TAT CTG TGT CGT ATC ATT GGA TTG GAA GTA TTT-C$_6$H$_{12}$-SH | 15 |
| System-VI | |
| A    TAC TTC CAA TCC AAT TCT TGT GTC GAT AGG TCG GTT GCT TTT TTT TTT TT-C$_6$H$_{12}$-SH<br>                           ||| ||| ||| ||| ||| ||| ||| ||| ||| ||| ||| ||<br>          3'-AGA ACA CAG CTA TCC AGC CAA CGA AAA AAA AAA AA-5' | 16<br><br>17 |
| B    ATT GGA TTG GAA GTA TCT TGT GTC GAT AGG TCG GTT GCT TTT TTT TTT TT-C$_6$H$_{12}$-SH<br>                           ||| ||| ||| ||| ||| ||| ||| ||| ||| ||| ||| ||<br>          3'-AGA ACA CAG CTA TCC AGC CAA CGA AAA AAA AAA AA-5' | 18<br><br>19 |

TABLE 2

Results of UV-Vis melting analysis for assembled aggregates

| System | Melting Analysis $T_m$ (° C.) |
|---|---|
| I | 63.4 (±0.5) |
| II | 64.0 (±0.5) |
| III | 64.3 (±0.6) |
| IV | 63.1 (±0.3) |
| V | a |
| VI | 66.3 (±0.5) | a Measurements indicate $T_m > 85°$ C.

As seen in FIG. 10, the crystal structure for system IV was determined using SAXS. The dotted lines (140) indicate the magnitude and position of S(q) peaks expected for a body-centered cubic (bcc) lattice of point scatterers. Experimental data taken at 30° C. (138) matches the theoretical predictions quite closely, indicating that the nanoparticles of system IV assemble into a three-dimensional crystal with bcc structure. A representation of a unit cell of the bcc structure (142) is shown in the inset. The proposed particle arrangement is indicated by light and dark spheres representing particles with complementary DNA linking sequences. Particles A have particles B as nearest neighbors, and vice versa; in other words the coordination sphere of particles A consists only of particles B and vice versa. The lattice parameter a for system IV is 34.8 nm at T=30° C. and 37.5 nm at T=57° C.

Figure 11:
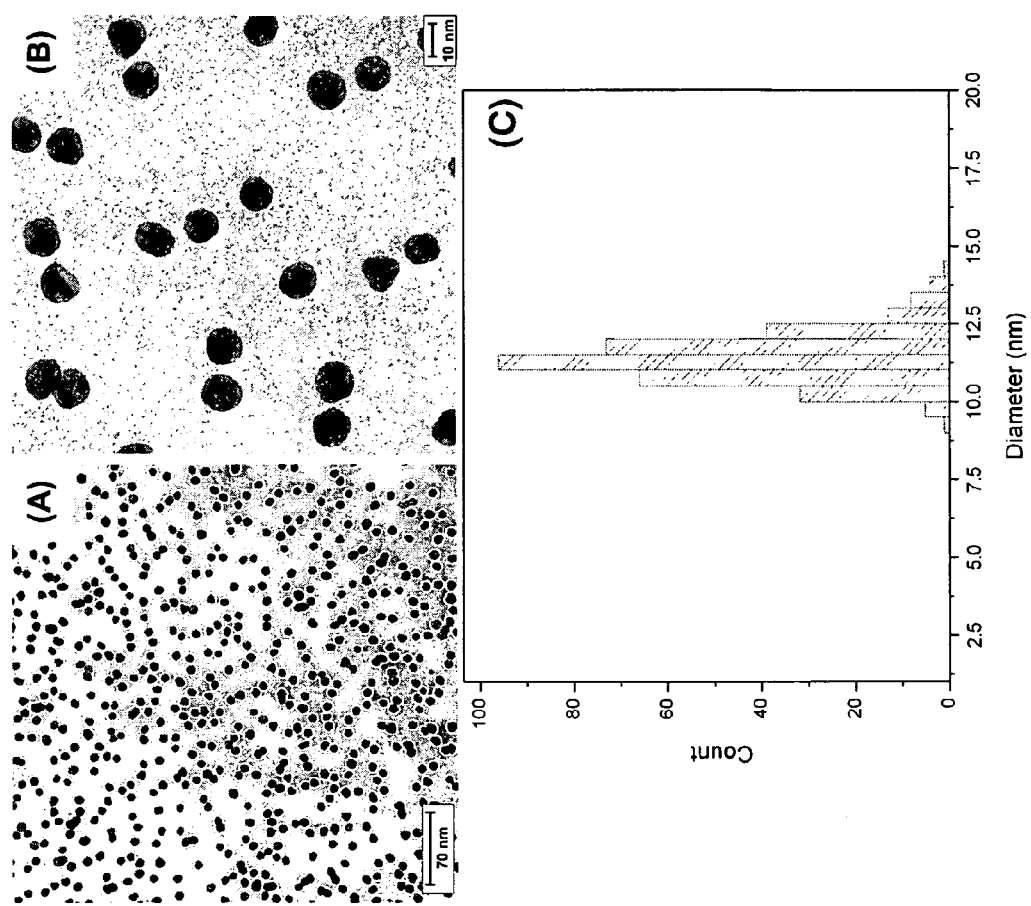
FIG. 11 contains a representative set of TEM images and statistical analysis of DNA-capped gold nanoparticles.

FIG. 11 contains a representative set of TEM images and statistical analysis of the DNA-capped gold nanoparticles used in systems I through VI. The scale bar in the left-hand micrograph equals 70 nm, while that in the right-hand image equals 10 nm. Statistical analysis of particle sizes yields a dimension of 11.4±1.0 nm for the nanoparticles (144).

Figure 12:
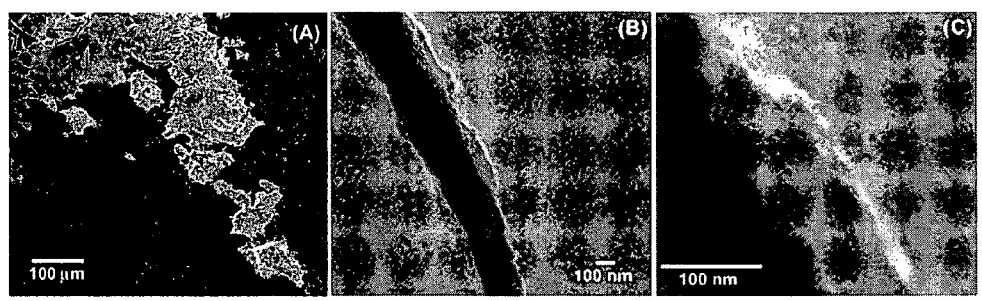
FIG. 12 contains a representative set of scanning electron microscopy (SEM) images collected from system IV after crystal formation.
Figure 13:
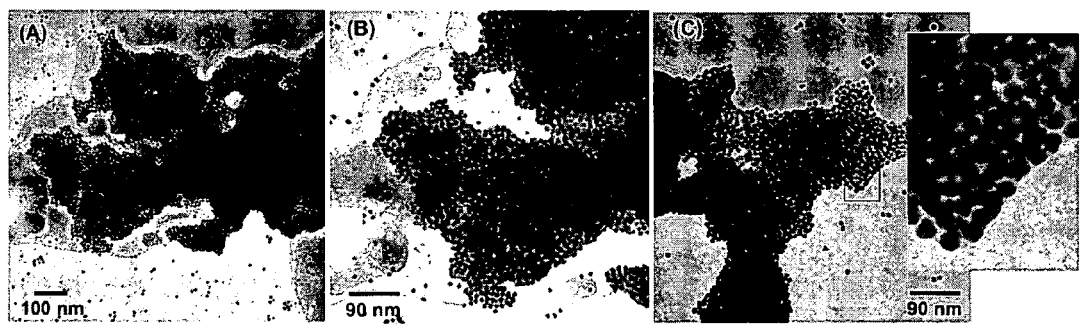
FIG. 13 contains a representative set of TEM images collected from system IV after crystal formation.

FIG. 12 contains a representative set of SEM images collected from system IV after crystal formation. The scale bar in the left-most SEM image equals 100 micrometers while those in the other two images correspond to 100 nanometers. Nanoparticles (146) appear light on the darker background of the substrate. FIG. 13, similarly, shows a representative set of TEM images collected from system IV after crystal formation. The scale bar in the left-most TEM image equals 100 nm while those in the other two images represent 90 nm. The area of the zoomed inset is shown by the box in the right-most micrograph. Again the nanoparticles (150) can be seen clearly.

Figures 14, 15:
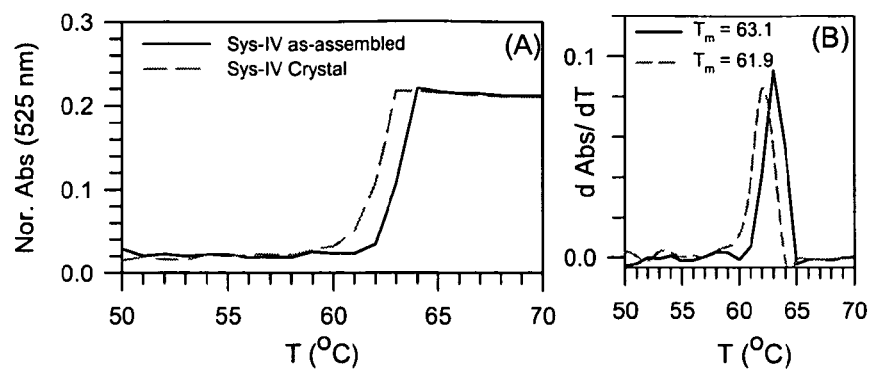
FIG. 14 shows a set of melting profiles for system IV aggregates in pre-annealing and crystallized states.
FIG. 15 shows the first derivative plots corresponding to FIG. 14.

FIG. 14 shows a set of melting profiles for system IV aggregates in pre-annealed and crystallized states, while their first derivatives with respect to temperature appear in FIG. 15. The solid lines correspond to the aggregates before annealing and the dashed lines to the crystallized structure. Analysis of the plots in FIG. 15 yields a melting temperature of 63° C. for the pre-annealed form and 62° C. for the crystalline form. Data was taken for aggregates in a solution of 10 mM phosphate buffer with 0.20 M NaCl and a pH of 7.1; the rate of temperature change was 1° C. per minute.

Figure 16:
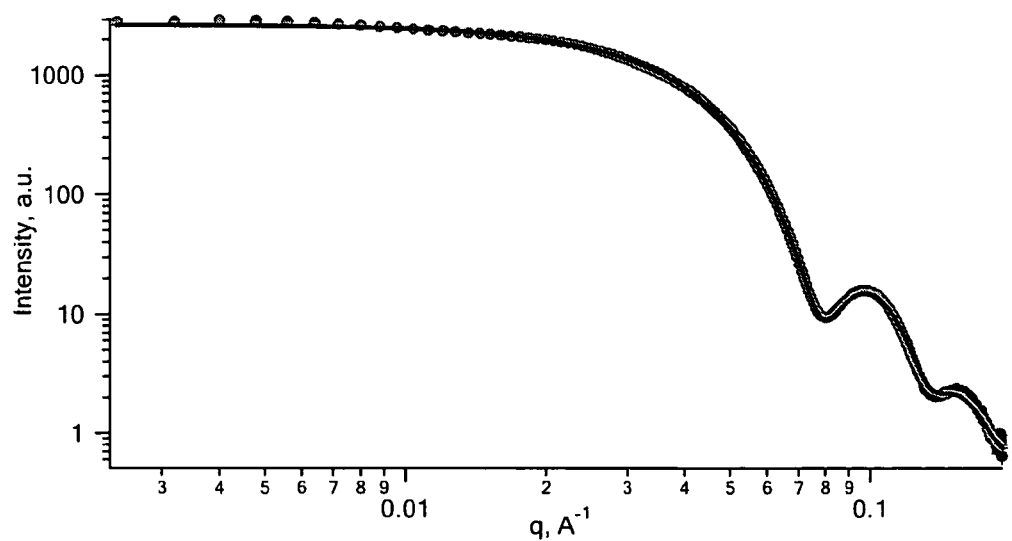
FIG. 16 depicts the scattering intensity for system IV at 71° C.

FIG. 16 depicts the scattering intensity for system IV at 71° C. as a function of q. Data is represented by solid symbols (160), while the solid line (162) represents fitting the data to predictions for spheroidal particles having a Gaussian size distribution. The fitted particle diameter is 11.5±1.2 nm, very close to the diameter of 11.4±1.0 nm as determined by TEM (FIG. 11)

Similar results may be achieved using particles of vastly different size and composition.

Example 4

Polystyrene Microparticles

Surface modification of polystyrene particles: Single-stranded 3'-primary amine-modified ssDNA with bases ranging from 30-200 bases were grafted onto carboxylated polystyrene colloidal spheres, 1.9 μm. In a typical modification, 0.15 wt % of particles were suspended and incubated with 15 μM DNA solution in 100 mM imidazole buffer pH 7.0 for three hours at 50° C. in the presence of 100 mM EDAC. The modified particles were cleaned 3 times in 0.5% SDS solution by successive centrifugation (at 800 g, 6 min) and supernatant exchange. Then, similarly, they were washed three times in hot (60° C.) deionized water and re-dispersed in 10 mM phosphate buffer, pH 7.7, for storage at 4° C.

The amount of non-complementary DNA on the surface, $f_N$, was controlled by changing the ratio of DNA concentrations of linker (L) [L] and neutral (N) [N] used in the grafting procedure, $f_N=[N]/([N]+[L])$. DNA-functionalization was carried out as for the case of gold nanoparticles. The DNA surface density was quantified by fluorescence measurements to be approximately 0.3 strands per 10 nm$^2$, or about 300,000 total ssDNA strands per microparticle.

For $f_N<0.50$, only large aggregates were observed, each containing thousands of particles. At $f_N$ between 0.50 and 0.90 the aggregate sizes decreased with increasing $f_N$, containing only clusters of several polystyrene (PS) particles. When $f_N$ reaches about 0.95, only isolated un-assembled PS were observed. Thus, the effect of a reduction in aggregate size with increasing $f_N$ points to the strong influence of osmotic repulsion, provided by the N ssDNA, in balancing the attractive interactions. Similar results were obtained for functionalized Au nanoparticles (AuNP), with significant decreases in aggregate growth as $f_N$ increased. The melting temperatures of the AuNP also decreased with increasing $f_N$.

Example 5

Latex Microparticles

Surface modification of latex particles: Latex spheres, about 1.9 μm, were prepared and their surface modified following the same procedure as for the polystyrene microparticles. The amount of non-complementary DNA on the surface, $f_N$, was again controlled by changing the ratio of DNA concentrations [L] and [A] used in the grafting procedure, $f_N=[N]/([N]+[L])$. DNA-functionalization was carried out as for the case of gold nanoparticles. The DNA surface density was quantified by fluorescence measurements.

Results as for the PS microparticles were observed in which aggregate size decreased with increasing $f_N$. In addition, the rate of assembly of aggregates was observed to decrease with increasing $f_N$. Furthermore, these results were observed in a large range of ionic strengths, 0 to 140 mM. However, for a given $f_N$, aggregate size increased with increasing ionic strength.

At dimensions of micrometers, the surface of latex and PS particles may be assumed to be flat with regard to both linking and neutral DNA. Thus similar results may be obtained for nano- and micro-objects attached by hybridization to larger particles and flat surfaces.

Example 6

Linker DNA-mediated Crystallization of Nanoparticles

Gold Nanoparticle(AuNP) Synthesis: Briefly, 1 mM HAuCl$_4$ aqueous solution was heated to a boil for 15~30 minutes. Then a 10 mL trisodium citrate solution in a concentration of 38 mM was added into the solution in one aliquot. Upon initial color changed to red, the solution was immediately quenched by $H_2O$, and then cooled naturally to room temperature. The solution was stored and protected from light. The Au concentration was calculated via an extinction coefficient of $1.0 \cdot 10^8$ L mole$^{-1}$ cm$^{-1}$.

DNA-Nanoparticle Modification: Typically, thiol-functionalized single-stranded oligonucleotides (ssDNA-A and ssDNA-B, see below for sequences) purchased as disulfides (from IDT Inc.) were first reduced by a dithiolthreitol (DTT) aqueous solution, followed by elution in a freshly purified cross-linked dextran gel column (G-25, Amersham Bioscience) with a phosphate buffer (pH=7.0). The DNA was quantified using UV-Vis analysis with the specific DNA extinction coefficient. The synthesized Au nanoparticles (AuNP) were then functionalized with ssDNA-A or ssDNA-B as described previously. The cleaning process was typically repeated at least 3 times. The final ssDNA-AuNP was dispersed in 0.3 M PBS. The number of ssDNA bound to each AuNP was estimated to be about 50.

The linker L30 and L70 were provided by IDT Inc. with PAGE purification and were used without further purification. The assembly was obtained by mixing equal mole amounts of ssDNA-AuNP-A and ssDNA-AuNP-B in a concentration of 20~40 nM, and Linker L30 or Linker L70 in a concentration of 0.2~0.8 μM. The sample was then heated to 65° C. and kept at that temperature for ten minutes, and then cooled down to room temperature for about two hours. The suspension solution was transferred to a capillary tube and left overnight to let sediment settle on the bottom of capillary tube. The sample was then ready for the measurements.

Instrumentation: Measurements in this example were carried out using the following instrumentation. This detail is provided for the clarity offered by using concrete examples rather for than endorsing any particular manufacturer; any instrumentation of similar capability may be used.

TEM: TEM experiments were carried out on a JEOL-1300 microscope operated at 120 kV. The samples were prepared by drop casting the solution onto a carbon coated copper grid and excess solution was then removed.

SEM: The sample was deposited on a cleaned silicon substrate and measured using a Hitachi S-4800 Scanning Electron Microscope with typical 1 kV voltage and 10 μA emission current.

SAXS: The SAXS experiments were performed at the National

Synchrotron Light Source (NSLS) X-21 beamline. The samples in buffer solution were contained in quartz capillary tubes. The temperature controller has an accuracy of ±0.01° C. and an overshoot ~0.2° C. at high temperature. The scattering data was collected with a CCD area detector after equilibration for ten minutes at each temperature. The scattering vector q is calibrated by using silver behenate.

DLS: The DLS measurements were conducted on a Malvern Zetasizer ZS instrument. The instrument is equipped with a 633 nm laser source, and a backscattering detector at 173°. Data was analyzed using the CONTIN method.

UV-Vis: UV-Vis spectra were collected on a Perkin-Elmer Lambda 35 spectrometer (200-900 nm).

Figure 17:
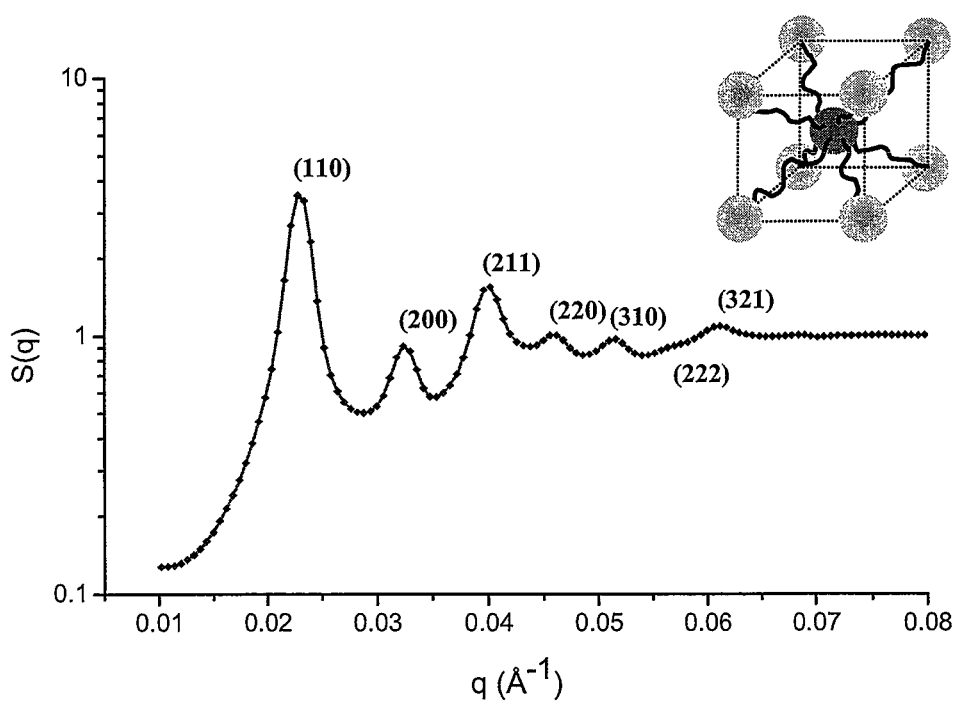
FIG. 17 shows the open bcc lattice formed in the DNA/Au nanoparticle hybrid system.

In this approach ssDNAs attached on the NPs are not complementary; linker DNA whose two ends are complementary to the respective ssDNA on NPs is needed (see the inset of FIG. 17). We have generated two sets of DNA/AuNP hybrid systems (Sys-L70 and Sys-L30) by mixing equal mole amounts of two types of ssDNA-capped AuNPs (denoted as ssDNA-AuNP-A and ssDNA-AuNP-B) and single-stranded linker DNA of different lengths in 0.3 M PBS buffer (10 mM phosphate buffer, 300 mM NaCl, pH≈7.0). The AuNP is 11.5±1.1 nm in diameter which can be deduced from electron microscopy and/or dynamic light scattering results.

The two types of capping ssDNAs are non-complementary: type A (A=5'-ATT GGAAGTGGATAA-$(T)_{15}C_3H_6$—SH)(SEQ ID NO: 20) and type B (B=HS—$C_6H_{12}$—$(T)_{15}$-TAACCTAAC CTTCAT-3')(SEQ ID NO: 21). Each has a 15-base outer recognition part and 15-b poly-T which serves as a spacer separating the recognition sequence from the AuNP surface. This spacer may be virtually any length, comprising at least 5-b poly-T (or poly-A or other non-interacting sequence, as desired). The linker DNAs are L70 (5'-TTATC-CACTTCCAAT-$(T)_{70}$-ATGAAGGTTAGGTTA-3')(SEQ ID NO: 22) and L30 (5'-TTATCCACTTCCAAT-$(T)_{30}$-ATGAAGGTTAGGTTA-3')(SEQ ID NO: 23), respectively. Each has a flexible poly-T and two ends complementary to the respective ends of ssDNA on AuNPs. The flexible poly-T sequence may be virtually any length at least 5 bases long. The melting temperature of the 15 bp dsDNA is around 60° C., measured by using a UV-Vis spectrophotometer.

FIG. 17 shows data supporting the formation of an open BCC lattice in the DNA/Au nanoparticle hybrid system. The data (points 202) agree well with the fit (204) to the structure factor for a bcc lattice. As seen in the inset, particles A (206) completely surround particles B (208) and the nearest neighbors of particles B are also only particles A. Although the DNA (210) prevents the particles from packing as densely as theoretically predicted, it does not account fully for the remarkably open crystal structure.

Figure 18:
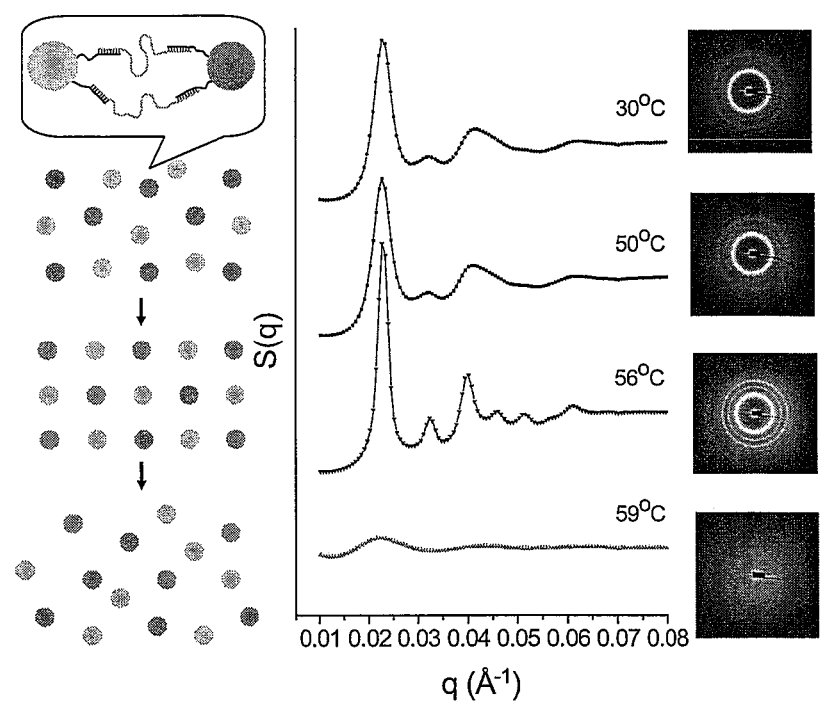
FIG. 18 shows a schematic illustration and representative temperature dependent two-dimensional (2D) SAXS patterns and respective extracted structure factors S(q) of Sys-L30 during heating.

FIG. 18 shows a schematic illustration and representative temperature dependent 2D SAXS patterns and respective extracted structure factors S(q) of Sys-L30 during heating. Two types of particles (212, 214) are linked by a linker (216) having a neutral region (222, 224). The structure is then linked along linking regions (218, 220). Two particle linkages are shown in FIG. 18. The degree of order increases from metastable (226) to crystalline (228) to disordered (230) as the temperature rises until the structure melts at around 59° C.

Figure 19:
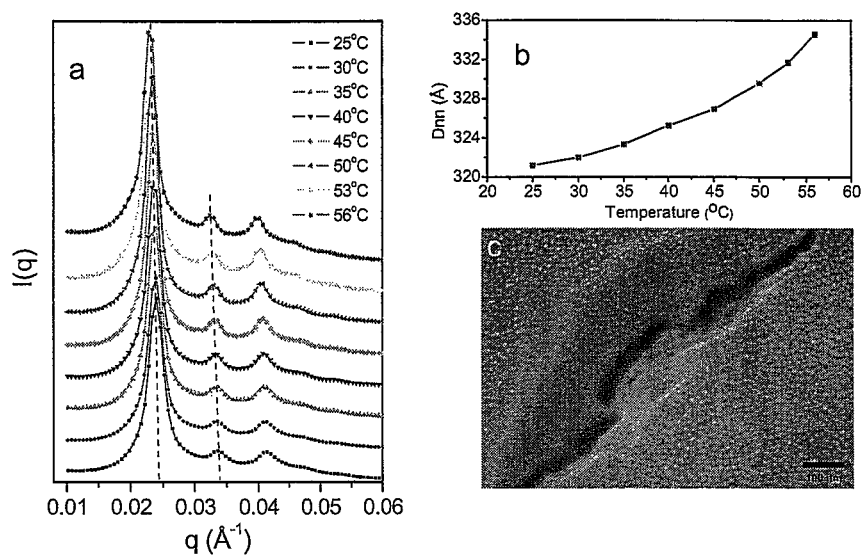
FIG. 19A shows temperature dependent SAXS patterns of Sys-L30 during cooling.
FIG. 19B shows the temperature dependent nearest neighbor distance during cooling.
FIG. 19C is a SEM image of Sys-L30 crystals after drying in air.

FIG. 19A shows temperature dependent SAXS patterns of Sys-L30 during cooling. The long-range order of the structure is maintained down to room temperature.

FIG. 19B shows the temperature dependent nearest neighbor distance decreasing during cooling. FIG. 19C is a SEM image of Sys-L30 crystals after drying in air. The black line (238) is a crack in the sample, while the dots (236) are the ordered nanoparticles. The scale bar is 100 mm.

Figure 20:
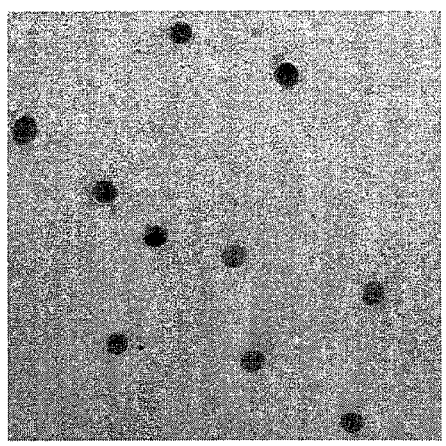
FIG. 20A is a representative TEM image of ssDNA-AuNPs.
FIG. 20B presents DLS results for uncapped AuNP, ssDNA-AuNP-A, and ssDNA-AuNP-B.
Figure 20:
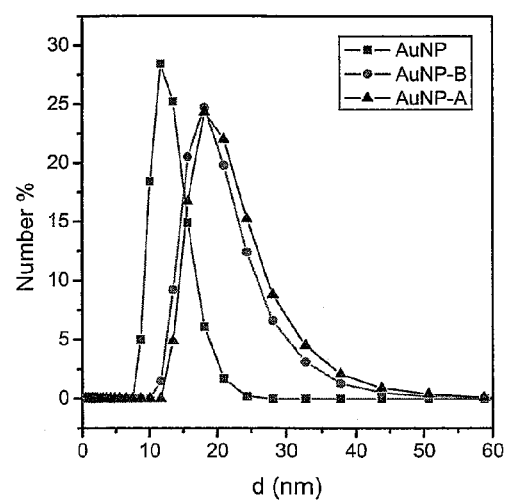

FIG. 20A is a representative TEM image of ssDNA-AuNPs (240) at high magnification. FIG. 20B presents DLS results for uncapped AuNP, ssDNA-AuNP-A, and ssDNA-AuNP-B. Both the ssDNA-AuNP-A and ssDNA-AuNP-B show a shift to larger diameters than the uncapped particles.

Figure 21:
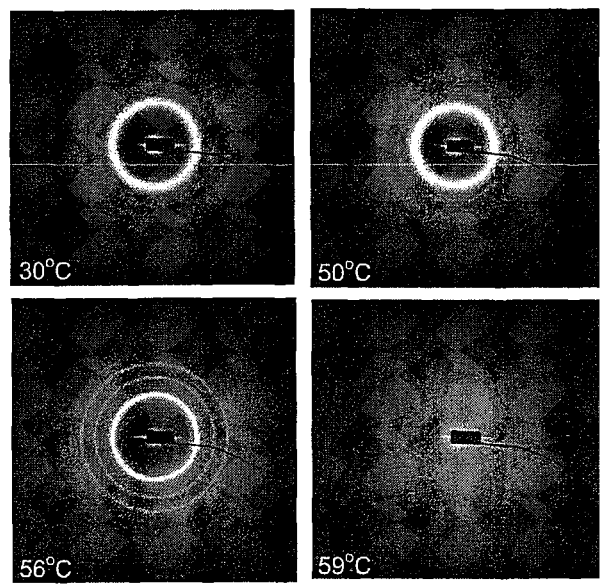
FIG. 21 presents representative temperature dependent 2D SAXS patterns of Sys-L70 during heating.

FIG. 21 presents representative temperature dependent 2D SAXS patterns of Sys-L70 during heating. The sharpness of the rings indicates the degree of order, which here increases from room temperature to a temperature just below the melting temperature of the DNA-capped structure.

While the foregoing description has been made with reference to individual embodiments of the invention, it should be understood that those skilled in the art, making use of the teaching herein, may propose various changes and modifications without departing from the invention in its broader aspects. For example, specific embodiments have been described using Au nanoparticles of an approximate diameter of 10 nm, but particles of other materials (metallic, semiconductive, magnetic, dielectric) of various dimensions may be substituted. Similarly, systems I-VI have been described as having linking and neutral segments of fixed size. In reality, the linking regions may contain from about 10 to about 200 bases, forming double-stranded linked regions with 10 to 200 base pairs, while the non-interacting neutral segments may contain from about 3 to about 200 bases. Again, although examples chosen refer to particles of the same material, mixed particles such as a metal and a semiconductor may be used. Microparticles having dimensions on the order of micrometers (0.1 μm to 100 μm) may be used in place of nanoparticles with dimensions on the order of nanometers (1 nm to 100 nm) (See examples 4 and 5.). As described with respect to system VI of the examples, neutral segments of the DNA sequences need not be single-stranded.

In addition, although the examples have, for concreteness, been described with reference to DNA functionalization, micro- and nano-objects can just as well be functionalized with RNA or PNA. Both RNA and PNA have the same addressable properties as does DNA, and similar melting temperatures and structure. PNA is artificial and is more resistant to degradation than DNA, allowing it to be used under conditions inimical to DNA, including in non-aqueous solvents. DNA and RNA, for example, may be used in concert. In this case, using catalytically active RNA strands to replace at least some of the neutral DNA may offer all of the kinetic benefits of combining neutral and hybridizing DNA while allowing the aggregates to take part in, or catalyze, additional reactions.

The foregoing description being illustrative, the invention is limited only by the claims appended hereto.

The invention claimed is:

1. A particle assemblage comprising:
   a plurality of a first type of particle functionalized with a first sequence of nucleic acid, the first sequence comprising a single-stranded segment of linking nucleic acid and a segment of spacer nucleic acid, wherein at least one segment of the spacer nucleic acid sequence is double-stranded;
   a plurality of a second type of particle functionalized with a second sequence of nucleic acid, the second sequence comprising a single-stranded segment of linking nucleic acid and a segment of spacer nucleic acid, wherein at least one segment of the spacer nucleic acid sequence of the second sequence is double-stranded;
   wherein the first and second sequences of nucleic acids are non-mutually complementary to each other;
   a linker having a third sequence of nucleic acid comprising
      a first segment of linking nucleic acid complementary to the segment of linking nucleic acid of the first sequence,
      a second segment of linking nucleic acid complementary to the segment of linking nucleic acid of the second sequence, and
      a segment of neutral nucleic acid having a poly-T DNA sequence of at least 5 bases, the segment of neutral nucleic acid separating the first segment of linking nucleic acid and second segment of linking nucleic acid;

wherein the first and second types of particle linked by hybridizing the first segment of linking nucleic acid of the linker to the complementary segment of linking nucleic acid of the first sequence and hybridizing the second segment of linking nucleic acid of the linker to the complementary segment of the linking nucleic acid of the second sequence, and the linked particles agglomerated to form the particle assemblage; and the particle assemblage displaying long-range crystalline order.

2. The particle assemblage of claim 1, wherein:
the first sequence of nucleic acid comprises a nucleic acid selected from the group consisting of RNA and PNA.

3. The particle assemblage of claim 1, wherein:
the first and second sequences of nucleic acid comprise DNA.

4. The particle assemblage of claim 3, wherein:
the neutral nucleic acid of the linker is double-stranded.

5. The particle assemblage of claim 4, wherein:
the spacer nucleic acid segments of the first and second sequences of nucleic acids each comprises at least 5 bases of poly-T DNA.

6. The particle assemblage of claim 1, wherein:
the long-range crystalline order extends about 10 interparticle spacings or more.

7. The particle assemblage of claim 1, wherein:
the long-range crystalline order is three-dimensional.

8. The particle assemblage of claim 1, wherein a plurality of segments of spacer nucleic acid are double-stranded.

9. The particle assemblage of claim 1, wherein:
the first and second types of particle have different compositions.

10. The particle assemblage of claim 1, wherein:
the first type of particle comprises micro-objects having dimensions of about 0.1 to about 100 micrometers.

11. The particle assemblage of claim 1, wherein
the first type of particle comprises nano-objects having dimensions of about 1 to about 100 nanometers.

12. The particle assemblage of claim 11, wherein the nano-objects have a character chosen from the group consisting of metallic, semiconductive, dielectric, and magnetic.

13. The particle assemblage of claim 12, wherein the nano-objects are gold nano-objects.

14. The particle assemblage of claim 11, further comprising:
a third type of nano-object functionalized with a fourth sequence of nucleic acid, the fourth sequence comprising a single-stranded segment of linking nucleic acid and a segment of spacer nucleic acid; and wherein the first and fourth types of particle are linked by a linker of double-stranded nucleic acid formed along the linking segments of the first and fourth sequences of nucleic acid.

15. The particle assemblage of claim 11, wherein:
the linker comprises a sequence of DNA of about 10 to about 200 base pairs;

the spacer segment of the first sequence of nucleic acid comprises a DNA spacer region comprising from about 3 to about 200 bases; and the spacer segment of the second sequence of nucleic acid comprises a DNA spacer region comprising from about 3 to about 200 bases.

16. The particle assemblage of claim 15, wherein:
the linker DNA comprises 15 base pairs;
the DNA spacer region of the first sequence comprises 35 bases; and
the DNA spacer region of the second sequence comprises 35 bases.

17. The particle assemblage of claim 1, wherein:
the first sequence of nucleic acid is SEQ ID NO: 6 and the second sequence of nucleic acid is SEQ ID NO: 7.

18. The particle assemblage of claim 1, wherein:
the first sequence of nucleic acid is SEQ ID NO: 8 and the second sequence of nucleic acid is SEQ ID NO: 9.

19. The particle assemblage of claim 1, wherein:
the first sequence of nucleic acid is SEQ ID NO: 10 and the second sequence of nucleic acid is SEQ ID NO: 11.

20. The particle assemblage of claim 1, wherein:
the first sequence of nucleic acid is SEQ ID NO: 12 and the second sequence of nucleic acid is SEQ ID NO: 13.

* * * * *

SEQUENCE LISTING

```
<160> NUMBER OF SEQ ID NOS: 23

<210> SEQ ID NO 1
<211> LENGTH: 30
<212> TYPE: DNA
<213> ORGANISM: Artificial Sequence
<220> FEATURE:
<223> OTHER INFORMATION: Thiol-functionalized single stranded
      oligonucleotide
<220> FEATURE:
<221> NAME/KEY: misc_feature
<222> LOCATION: (30)..(30)
<223> OTHER INFORMATION: -C3H6-SH

<400> SEQUENCE: 1
tacttccaat ccaattttt tttttttttt                                  30

<210> SEQ ID NO 2
<211> LENGTH: 30
<212> TYPE: DNA
<213> ORGANISM: Artificial Sequence
<220> FEATURE:
<223> OTHER INFORMATION: Thiol-functionalized single stranded
      oligonucleotide
<220> FEATURE:
<221> NAME/KEY: misc_feature
<222> LOCATION: (30)..(30)
<223> OTHER INFORMATION: -C3H6-SH

<400> SEQUENCE: 2
attggattgg aagtattttt tttttttttt                                  30

<210> SEQ ID NO 3
<211> LENGTH: 30
<212> TYPE: DNA
<213> ORGANISM: Artificial Sequence
<220> FEATURE:
<223> OTHER INFORMATION: Thiol-functionalized single stranded
      oligonucleotide
<220> FEATURE:
<221> NAME/KEY: misc_feature
<222> LOCATION: (30)..(30)
<223> OTHER INFORMATION: -C3H6-SH

<400> SEQUENCE: 3
tacttccaat ccaattttt tttttttttt                                  30

<210> SEQ ID NO 4
<211> LENGTH: 30
<212> TYPE: DNA
<213> ORGANISM: Artificial Sequence
<220> FEATURE:
```

```
<223> OTHER INFORMATION: Thiol-functionalized single stranded
      oligonucleotide
<220> FEATURE:
<221> NAME/KEY: misc_feature
<222> LOCATION: (30)..(30)
<223> OTHER INFORMATION: -C3H6-SH

<400> SEQUENCE: 4
attggattgg aagtatttt tttttttttt                                30

<210> SEQ ID NO 5
<211> LENGTH: 30
<212> TYPE: DNA
<213> ORGANISM: Artificial Sequence
<220> FEATURE:
<223> OTHER INFORMATION: Thiol-functionalized single stranded
      oligonucleotide
<220> FEATURE:
<221> NAME/KEY: misc_feature
<222> LOCATION: (30)..(30)
<223> OTHER INFORMATION: -C3H6-SH

<400> SEQUENCE: 5
ttctctacac tgtcttttt tttttttttt                                30

<210> SEQ ID NO 6
<211> LENGTH: 18
<212> TYPE: DNA
<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (18)..(18)
<223> OTHER INFORMATION: -C6H12-SH

<400> SEQUENCE: 6
tacttccaat ccaatttt                                            18

<210> SEQ ID NO 7
<211> LENGTH: 18
<212> TYPE: DNA
<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (18)..(18)
<223> OTHER INFORMATION: -C6H12-SH

<400> SEQUENCE: 7
attggattgg aagtattt                                            18

<210> SEQ ID NO 8
<211> LENGTH: 30
<212> TYPE: DNA
<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (30)..(30)
<223> OTHER INFORMATION: -C3H6-SH

<400> SEQUENCE: 8
tacttccaat ccaatttttt tttttttttt                               30

<210> SEQ ID NO 9
<211> LENGTH: 30
<212> TYPE: DNA
```

<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (30)..(30)
<223> OTHER INFORMATION: -C3H6-SH

<400> SEQUENCE: 9
attggattgg aagtattttt tttttttttt                                    30

<210> SEQ ID NO 10
<211> LENGTH: 50
<212> TYPE: DNA
<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (50)..(50)
<223> OTHER INFORMATION: -C6H12-SH

<400> SEQUENCE: 10
tacttccaat ccaattcttg tgtcgatagg tcggttgctt tttttttttt              50

<210> SEQ ID NO 11
<211> LENGTH: 30
<212> TYPE: DNA
<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (30)..(30)
<223> OTHER INFORMATION: -C3H6-SH

<400> SEQUENCE: 11
attggattgg aagtattttt tttttttttt                                    30

<210> SEQ ID NO 12
<211> LENGTH: 50
<212> TYPE: DNA
<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (50)..(50)
<223> OTHER INFORMATION: -C6H12-SH

<400> SEQUENCE: 12
tacttccaat ccaattcttg tgtcgatagg tcggttgctt tttttttttt              50

<210> SEQ ID NO 13
<211> LENGTH: 50
<212> TYPE: DNA
<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (50)..(50)
<223> OTHER INFORMATION: -C6H12-SH

<400> SEQUENCE: 13
attggattgg aagtatcttg tgtcgatagg tcggttgctt tttttttttt              50

<210> SEQ ID NO 14
<211> LENGTH: 33
<212> TYPE: DNA

<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (33)..(33)
<223> OTHER INFORMATION: -C6H12-SH

<400> SEQUENCE: 14
tacttccaat ccaatgatac gacacagata ttt                             33

<210> SEQ ID NO 15
<211> LENGTH: 33
<212> TYPE: DNA
<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (33)..(33)
<223> OTHER INFORMATION: -C6H12-SH

<400> SEQUENCE: 15
tatctgtgtc gtatcattgg attggaagta ttt                             33

<210> SEQ ID NO 16
<211> LENGTH: 50
<212> TYPE: DNA
<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (50)..(50)
<223> OTHER INFORMATION: -C6H12-SH

<400> SEQUENCE: 16
tacttccaat ccaattcttg tgtcgatagg tcggttgctt tttttttttt            50

<210> SEQ ID NO 17
<211> LENGTH: 35
<212> TYPE: DNA
<213> ORGANISM: Artificial Sequence
<220> FEATURE:
<223> OTHER INFORMATION: single-stranded oligonucleotide

<400> SEQUENCE: 17
aaaaaaaaaa aagcaaccga cctatcgaca caaga                           35

<210> SEQ ID NO 18
<211> LENGTH: 50
<212> TYPE: DNA
<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (50)..(50)
<223> OTHER INFORMATION: -C6H12-SH

<400> SEQUENCE: 18
attggattgg aagtatcttg tgtcgatagg tcggttgctt tttttttttt            50

<210> SEQ ID NO 19
<211> LENGTH: 35
<212> TYPE: DNA
<213> ORGANISM: Artificial Sequence
<220> FEATURE:
<223> OTHER INFORMATION: single-stranded oligonucleotide -continued

```
<400> SEQUENCE: 19
aaaaaaaaaa aagcaaccga cctatcgaca caaga                                35

<210> SEQ ID NO 20
<211> LENGTH: 30
<212> TYPE: DNA
<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (30)..(30)
<223> OTHER INFORMATION: -C3H6-SH

<400> SEQUENCE: 20
attggaagtg gataattttt tttttttttt                                      30

<210> SEQ ID NO 21
<211> LENGTH: 30
<212> TYPE: DNA
<213> ORGANISM: Artificial Sequence
<220> FEATURE:
<223> OTHER INFORMATION: Thiol-modified single-stranded oligonucleotide
<220> FEATURE:
<221> NAME/KEY: misc_feature
<222> LOCATION: (1)..(1)
<223> OTHER INFORMATION: HS-C6H12-

<400> SEQUENCE: 21
tttttttttt tttttaacc taaccttcat                                       30

<210> SEQ ID NO 22
<211> LENGTH: 100
<212> TYPE: DNA
<213> ORGANISM: Artificial Sequence
<220> FEATURE:
<223> OTHER INFORMATION: Linker DNA L70

<400> SEQUENCE: 22
ttatccactt ccaattttt ttttttttt ttttttttt tttttttttt                   60 tttttttttt tttttttttt tttttatgaa ggttaggtta                          100

<210> SEQ ID NO 23
<211> LENGTH: 60
<212> TYPE: DNA
<213> ORGANISM: Artificial Sequence
<220> FEATURE:
<223> OTHER INFORMATION: Linker DNA L30

<400> SEQUENCE: 23
ttatccactt ccaattttt ttttttttt ttttttttt tttttatgaa ggttaggtta        60
```